United States Patent [19]

Watthey

[11] Patent Number: 4,537,885
[45] Date of Patent: * Aug. 27, 1985

[54] CERTAIN BENZAZOCINONE AND BENZAZONINONE DERIVATIVES

[75] Inventor: Jeffrey W. H. Watthey, Chappaqua, N.Y.

[73] Assignee: Ciba Geigy Corporation, Ardsley, N.Y.

[ * ] Notice: The portion of the term of this patent subsequent to Sep. 11, 2001 has been disclaimed.

[21] Appl. No.: 578,454

[22] Filed: Feb. 9, 1984

Related U.S. Application Data

[63] Continuation-in-part of Ser. No. 465,696, Feb. 10, 1983, Pat. No. 4,470,988.

[51] Int. Cl.$^3$ .................. A61K 31/395; C07D 225/06
[52] U.S. Cl. .............. 514/183; 260/239.3 B; 260/239.3 T
[58] Field of Search .............. 260/239.3 B, 239.3 T; 424/244, 267, 274, 263

[56] References Cited

U.S. PATENT DOCUMENTS

| | | | |
|---|---|---|---|
| 3,661,927 | 5/1972 | Zivkovic | 260/239 BB |
| 3,748,321 | 7/1973 | Krapcho | 260/239 BB |
| 4,322,439 | 3/1982 | Klemm et al. | 562/456 |
| 4,410,520 | 10/1983 | Watthey | 260/239.3 B |
| 4,470,988 | 9/1984 | Watthey | 424/263 |
| 4,473,575 | 9/1984 | Watthey | 260/239.3 D |

FOREIGN PATENT DOCUMENTS

| | | | |
|---|---|---|---|
| 0046292 | 2/1982 | European Pat. Off. | 260/239.3 R |
| 0046289 | 2/1982 | European Pat. Off. | 260/239.3 B |
| 0046291 | 2/1982 | European Pat. Off. | 260/239.3 R |
| 0107095 | 5/1984 | European Pat. Off. | 260/239.3 B |
| 6902595 | 8/1969 | Netherlands | 260/234 BB |

OTHER PUBLICATIONS

Saito, I. J. Am. Chem. Society, 101, 7332, (1979).

*Primary Examiner*—Robert T. Bond
*Attorney, Agent, or Firm*—Norbert Gruenfeld

[57] ABSTRACT

Variously substituted 1-carboxymethyl-3-(carboxymethylamino)-benzazocin-2-one and benzazonin-2-one derivatives are disclosed as angiotensin converting enzyme inhibitors and anti-hypertensive agents. Synthesis of, pharmaceutical compositions and methods of treatment utilizing such compounds are included.

11 Claims, No Drawings

CERTAIN BENZAZOCINONE AND BENZAZONINONE DERIVATIVES

CROSS REFERENCE TO RELATED APPLICATION

This is a continuation-in-part application of application Ser. No. 465,696 filed Feb. 10, 1983 now U.S. Pat. No. 4,470,988.

SUMMARY OF THE INVENTION

The present invention is based upon the discovery that certain substituted 3-amino-1-benzazocin-2-one-1-alkanoic acid and 3-amino-1-benzazonin-2-one-1-alkanoic acid derivatives represent potent angiotensin-converting enzyme (ACE) inhibitors.

The foregoing attributes render the compounds of this invention particularly useful when administered, alone or in combination, to mammals, e.g. for the treatment or prevention of diseases responsive to inhibition of angiotensin converting enzyme e.g., cardiovascular disorders such as hypertension and cardiac conditions such as congestive heart failure.

DETAILED DISCLOSURE

This invention relates to the novel heterocyclic compounds of formula I, and derivatives useful as angiotensin-converting enzyme inhibitors, processes for preparing same, pharmaceutical compositions comprising said compounds, and methods of treating diseases responsive to inhibition of angiotensin-converting enzyme by administration of said compounds and compositions to mammals.

The compounds of the invention are characterized by the general formula

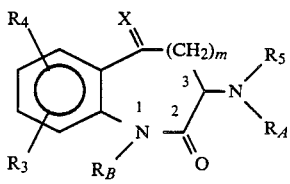

wherein $R_A$ and $R_B$ are radicals of the formula

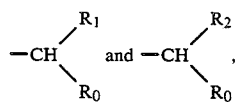

respectively, in which $R_o$ is carboxy or a functionally modified carboxy;

$R_1$ is hydrogen, lower alkyl, amino(lower) alkyl, aryl, aryl (lower) alkyl, cycloalkyl, cycloalkyl (lower) alkyl, acylamino (lower)alkyl, mono- or di-(lower) alkylamino(lower) alkyl, lower alkylthio (lower) alkyl, carboxy (lower) alkyl, esterified carboxy (lower) alkyl, carbamoyl (lower) alkyl, N-substituted carbamoyl (lower) alkyl, hydroxy (lower) alkyl, etherified or acylated hydroxy (lower) alkyl, aryloxy (lower) alkyl, aryl-(thio-, sulfinyl-, or sulfonyl-) lower alkyl, aryl-N-(lower) alkylamino (lower) alkyl, or arylamino (lower) alkyl;

$R_2$ is hydrogen or lower alkyl;

$R_3$ and $R_4$, each independently, represent hydrogen, lower alkyl, lower alkoxy, lower alkanoyloxy, hydroxy, halogen, trifluoromethyl, or $R_3$ and $R_4$ taken together represent lower alkylenedioxy;

$R_5$ is hydrogen or lower alkyl; m is 2 or 3; and

X represents oxo, two hydrogens, or one hydroxy or acylated hydroxy together with one hydrogen; and wherein the carbocyclic ring may also be hexahydro; and salts and complexes thereof.

The functionally modified carboxyl group in the meaning of the symbol $R_o$ is e.g. an esterified carboxyl group or a carbamoyl group optionally substituted on the nitrogen atom.

More specifically one or both of $R_o$ represented by $COR_6$ in radical $R_A$ and represented by $COR_7$ in radical $R_B$ independently represent carboxy, esterified carboxy, carbamoyl or substituted carbamoyl.

The salts and complexes of the compounds of formula I are derived from those compounds which have salt forming properties and are preferably pharmaceutically acceptable salts and complexes.

A carboxyl group $R_o$ is represented by $COR_6$ (in radical $R_A$) wherein $R_6$ is hydroxy or $COR_7$ (in radical $R_B$) wherein $R_7$ is hydroxy.

An esterified carboxyl group $R_o$ is especially one in which the esterifying radical represents optionally substituted lower alkyl or optionally substituted phthalidyl and is represented by the partial formula —$COR_6$ (in radical $R_A$) or the partial formula —$COR_7$ (in radical $R_B$)

wherein one or both of $R_6$ and $R_7$ represent lower alkoxy; (amino, mono- or di-lower alkylamino)-substituted lower alkoxy; carboxy-substituted lower alkoxy, e.g. α-carboxy-substituted lower alkoxy; lower alkoxycarbonyl-substituted lower alkoxy, e.g. α-lower alkoxycarbonyl-substituted lower alkoxy; aryl-substituted lower alkoxy, e.g. optionally substituted benzyloxy or pyridylmethoxy; (hydroxy, lower alkanoyloxy or lower alkoxy)-substituted lower alkoxy, e.g. pivaloyloxymethoxy; (hydroxy, lower alkanoyloxy or lower alkoxy)-substituted lower alkoxymethoxy; bicycloalkoxycarbonyl-substituted lower alkoxy, e.g. bicyclo[2,2,1]-heptyloxycarbonyl-substituted lower alkoxy, especially bicyclo[2,2,1]heptyloxycarbonyl-substituted methoxy; 3-phthalidoxy; (lower alkyl, lower alkoxy, halo)-substituted 3-phthalidoxy.

An optionally N-substituted carbamoyl group $R_o$ is especially one which is represented by the partial formula —$COR_6$ (in radical $R_A$) or the partial formula —$COR_7$ (in radical $R_B$)

wherein one or both of $R_6$ and $R_7$ represent amino; lower alkylamino; di-lower alkylamino; di-lower alkylamino in which both alkyl groups are linked by a carbon to carbon bond and together with the amino nitrogen form a 5-, 6- or 7-membered heterocyclic ring, e.g. pyrrolidino, piperidino, or perhydroazepino; (amino or acylamino)-substituted lower alkylamino; α-(carboxy or lower alkoxycarbonyl)-substituted lower alkylamino; aryl substituted lower alkylamino in which aryl is preferably phenyl or indolyl and which can be substituted on the α-carbon by carboxy or lower alkoxycarbonyl.

Furthermore, the terms esterified carboxy and N-substituted carbamoyl, as such appear in esterified carboxy(lower) alkyl and N-substituted carbamoyl (lower)alkyl within the definition of $R_1$, may have any of the meanings cited above for said terms.

Any prodrug derivatives of compounds of this invention e.g. any pharmaceutically acceptable esters and amides of the mono- or di-carboxylic acids of this invention that may be convertible by solvolysis or under physiological conditions to the said carboxylic acids e.g. esters and amides cited above, represent a particular object of the invention.

Said esters are preferably, e.g., the straight chain or branched lower alkyl esters unsubstituted or suitably substituted such as the pivaloyloxymethyl, bornyloxycarbonylmethyl, benzyl, pyridylmethyl, α-carboxyethyl or suitably esterified α-carboxyethyl esters, and the like.

Said amides are preferably e.g. simple primary and secondary amides and amides derived from the amino acids or derivatives thereof, such as the amides derived from alanine, phenylalanine and the like.

More particularly, the invention relates to compounds of formula IA

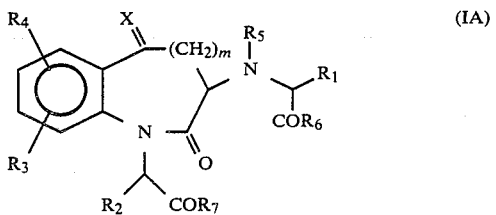

wherein the carbocyclic ring may also be hexahydro;

$R_1$ is hydrogen, lower alkyl, amino(lower)alkyl, aryl, aryl (lower) alkyl, cycloalkyl, cycloalkyl (lower) alkyl, acylamino (lower) alkyl, mono- or di- (lower) alkylamino(lower) alkyl, lower alkylthio (lower) alkyl, carboxy (lower) alkyl, esterified carboxy (lower) alkyl, carbamoyl (lower) alkyl, N-substituted carbamoyl (lower) alkyl, hydroxy (lower) alkyl, etherified or acylated hydroxy (lower) alkyl, aryloxy (lower) alkyl, arylthio (lower) alkyl, aryl-N-(lower) alkylamino (lower) alkyl, or arylamino(lower) alkyl;

$R_2$ and $R_5$ represent hydrogen or lower alkyl;

$R_3$ and $R_4$ represent hydrogen, lower alkyl, lower alkoxy, lower alkanoyloxy, hydroxy, halogen, trifluoromethyl; or $R_3$ and $R_4$ taken together represent lower alkylenedioxy;

X represents oxo, two hydrogens, or one hydroxy or acylated hydroxy group and one hydrogen;

m is 2 or 3;

$R_6$ and $R_7$ independently represent hydroxy, amino, mono- or di-(lower)alkylamino, lower alkoxy, aryl(-lower)alkoxy, lower alkanoyloxymethoxy, (amino, mono- or di-lower alkylamino, carboxy, or lower alkoxycarbonyl)-lower alkoxy; or the pharmaceutically acceptable salts or complexes thereof.

A more specific embodiment of this invention relates to compounds of formula IA wherein $R_1$ is hydrogen, lower alkyl, amino(lower)alkyl, aryl, aryl(lower)alkyl, cycloalkyl(lower)alkyl; and wherein within the above definitions aryl represents phenyl unsubstituted or mono- or di-substituted by lower alkyl, lower alkoxy, lower alkylenedioxy, lower alkanoyloxy, hydroxy, halogen or trifluoromethyl; and cycloalkyl contains 3 to 8 carbons; X, m and $R_2$ to $R_7$ are as defined above; or the pharmaceutically acceptable salts or complexes thereof; or said compounds wherein the carbocyclic ring is hexahydro.

A further embodiment of this invention relates to compounds of formula IA wherein $R_1$ is aryl(lower) alkyl where aryl represents indolyl, carboxy(lower) alkyl, lower alkoxycarbonyl (lower) alkyl, hydroxy (lower) alkyl, lower alkylthio(lower) alkyl, acylamino(-lower) alkyl; aryloxy (lower) alkyl or arylthio (lower) alkyl; X, m and $R_2$ to $R_7$ are as defined above; or the pharmaceutically acceptable salts or complexes thereof; or said compounds wherein the carboxylic ring is hexahydro.

Preferred embodiments of this invention relate to compounds of formula IA wherein the carbocyclic ring may also be hexahydro; $R_1$ is hydrogen, lower alkyl, amino(lower)alkyl, acylamino(lower) alkyl, aryl(lower-)alkyl where aryl represents phenyl unsubstituted or mono- or disubstituted by lower alkyl, hydroxy, lower alkoxy, lower alkylenedioxy, lower alkanoyloxy, halogen or trifluoromethyl;

$R_2$ and $R_5$ are hydrogen or lower alkyl;

$R_3$ and $R_4$ are hydrogen, lower alkoxy, lower alkyl, halogen or trifluoromethyl; or $R_3$ and $R_4$ taken together represent alkylenedioxy;

X represents oxo, one hydroxy or acylated hydroxy and one hydrogen, or 2 hydrogens; m is 2 or 3;

$R_6$ and $R_7$ independently represent hydroxy, amino, lower alkoxy, phenyl(lower)alkoxy, lower alkoxycarbonyl(lower)alkoxy;

or pharmaceutically acceptable salts thereof.

Especially preferred are compounds of formula IA, wherein $R_1$ is hydrogen, lower alkyl, amino(lower)alkyl, aryl(lower) alkoxycarbonylamino (lower) alkyl or aryl(lower)alkyl where aryl represents phenyl unsubstituted or mono-substituted by lower alkyl, hydroxy, lower alkoxy, lower alkanoyloxy, halogen or trifluoromethyl;

$R_2$ and $R_5$ are hydrogen or lower alkyl;

$R_3$ and $R_4$ are hydrogen, lower alkoxy, lower alkyl, halogen, or trifluoromethyl; or $R_3$ and $R_4$ taken together represent lower alkylenedioxy;

X represents oxo, one hydroxy or lower alkanoyloxy and one hydrogen, or 2 hydrogens; m is 2 or 3;

$R_6$ and $R_7$ independently represent hydroxy, amino, lower alkoxy, phenyl(lower)alkoxy, lower alkoxycarbonyl(lower)alkoxy;

or pharmaceutically acceptable salts thereof; or said compounds wherein the carbocyclic ring is hexahydro.

Particularly preferred are compounds of formula IA wherein $R_1$ is hydrogen, lower alkyl, ω-amino(lower)alkyl, ω-arylmethoxycarbonylamino-(lower) alkyl, aryl(-lower) alkyl where aryl represents phenyl unsubstituted or mono-substituted by lower alkyl, hydroxy, lower alkoxy, lower alkanoyloxy, halogen or trifluoromethyl;

$R_2$ and $R_5$ are hydrogen or lower alkyl;

$R_3$ is hydrogen;

$R_4$ is hydrogen, lower alkoxy, lower alkyl, halogen, or trifluoromethyl;

X represents oxo, one hydroxy or lower alkanoyloxy and one hydrogen, or 2 hydrogens; m is 2 or 3;

$R_6$ and $R_7$ independently represent hydroxy, amino, lower alkoxy, phenyl(lower)alkoxy, lower alkoxycarbonyl(lower)alkoxy;

or pharmaceutically acceptable salts thereof; or said compounds wherein the carbocyclic ring is hexahydro.

Especially preferred are compounds of formula IA wherein $R_1$ is hydrogen, methyl, ethyl, isopropyl, ω-aminopropyl, ω-aminobutyl, ω-(benzyloxycarbonylamino)propyl, ω-(benzyloxycarbonylamino)butyl, aryl-(methyl, ethyl, propyl) where aryl represents phenyl unsubstituted or substituted by one methyl, hydroxy, methoxy, methylenedioxy, acetoxy, chloro or trifluoromethyl group;

$R_2$ and $R_5$ are hydrogen or methyl;

$R_3$ and $R_4$ represent hydrogen, methoxy, methyl, chloro or trifluoromethyl;

X represents oxo, one hydroxy or one acetoxy and one hydrogen, or 2 hydrogens; m is 2 or 3;

$R_6$ and $R_7$ independently represent hydroxy, amino, ethoxy, methoxy, benzyloxy, ethoxycarbonylmethoxy or pivaloyloxymethoxy;

or pharmaceutically acceptable salts thereof; or said compounds wherein the carbocyclic ring is hexahydro.

Very much preferred are compounds of formula IB

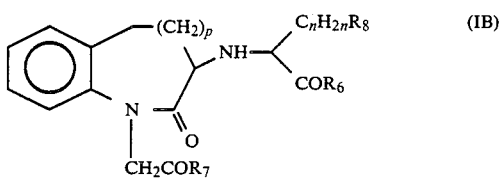

wherein the carboxylic ring may also be hexahydro;

n represents an integer from 1 to 4; p is the integer 3 or 4;

$R_8$ is hydrogen, amino, benzyloxycarbonylamino, phenyl unsubstituted or monosubstituted by lower alkyl, lower alkoxy, lower alkanoyloxy, halogen, hydroxy, or trifluoromethyl;

$R_6$ and $R_7$ independently represent hydroxy, lower alkoxy of up to 4 carbon atoms, benzyloxy, amino;

or pharmaceutically acceptable salts thereof.

Preferred in turn are compounds of formula IB wherein $C_nH_{2n}$ represents ethylene; $R_8$ represents phenyl or phenyl monosubstituted by lower alkoxy with up to 4 carbon atoms, lower alkyl with up to 4 carbon atoms, halogen or trifluoromethyl;

$R_6$ and $R_7$ independently represent hydroxy or lower alkoxy with up to 4 carbon atoms; p is the integer 3 or 4;

or pharmaceutically acceptable salts thereof; or said compounds wherein the carbocyclic ring is hexahydro.

Also preferred are compounds of formula IB wherein $C_nH_{2n}$ represents n-propylene or n-butylene; $R_8$ represents amino or benzyloxycarbonylamino; $R_6$ and $R_7$ independently represent hydroxy or lower alkoxy with up to 4 carbon atoms; p is the integer 3 or 4; or pharmaceutically acceptable salts thereof; or said compounds wherein the carboxyclic ring is hexahydro.

Further preferred are the said compounds of formula 1B wherein $(CH_2)_p$ represents propylene.

The present invention also relates to the stereoisomers of compounds of formula I. A number of racemates are obtainable when, e.g. in formula IA at least one of $R_1$ and $R_2$ is not hydrogen and/or X represents H(OH) or H(acylated OH). Furthermore, the compounds of the invention in which the carbocyclic ring is hexahydro may also exist as the isomers with either a cis or trans ring junction.

The individual enantiomers of said racemates may in turn be obtained. Certain specific said isomers are preferred as angiotensin-converting enzyme inhibitors.

Preferred are said compounds in which the asymmetric ring carbon (position 3) bearing the substituted amino group is of the (S)-configuration. Further preferred are said compounds in which the side chain asymmetric carbon atom bearing the $COR_6$ group is of the (S)-configuration.

Outstanding are compounds of formula IC

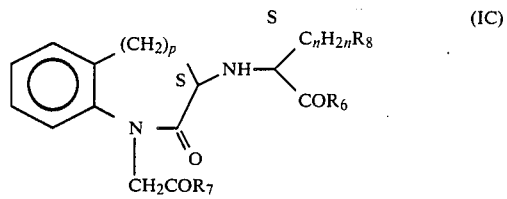

wherein S represents the chirality, n represents an integer from 1 to 4; p is the integer 3 or 4;

$R_8$ is hydrogen, amino, benzyloxycarbonylamino, phenyl unsubstituted or monosubstituted by lower alkyl, lower alkoxy, lower alkanoyloxy, halogen, hydroxy, or trifluoromethyl;

$R_6$ and $R_7$ independently represent hydroxy, lower alkoxy of up to 4 carbon atoms, benzyloxy, amino; or pharmaceutically acceptable salts thereof.

Preferred in turn are said compounds of formula IB and IC wherein $(CH_2)_p$ represents propylene.

The general definitions used herein have the following meanings within the scope of the present invention.

Aryl represents a carbocyclic or heterocyclic aromatic radical preferably being phenyl, unsubstituted or mono- or di-substituted by lower alkyl, lower alkoxy, lower alkylenedioxy, lower alkanoyloxy, hydroxy, halogen or trifluoromethyl; indolyl, advantageously 3-indolyl; or indolyl, advantageously 3-indolyl, substituted by lower alkyl, lower alkoxy, lower alkylenedioxy, lower alkanoyloxy, hydroxy, halogen or trifluoromethyl respectively.

The term cycloalkyl represents a cyclic hydrocarbon radical which preferably contains 3 to 8 carbons and is, for example, cyclopentyl or cyclohexyl.

The term aryl(lower)alkyl represents preferably benzyl, 1- or 2-phenylethyl, 1-, 2- or 3-phenylpropyl, 1-, 2-, 3- or 4-phenylbutyl, wherein the phenyl ring is unsubstituted or mono- or disubstituted by lower alkyl, hydroxy, lower alkoxy, lower alkylenedioxy, lower alkanoyloxy, halogen or trifluoromethyl; also indolylmethyl advantageously 3-indolylmethyl, 1- or 2-indolylethyl advantageously 2-(3-indolyl)ethyl.

The term cycloalkyl(lower)alkyl represents preferably 1 or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)-butyl.

The term "lower" referred to above and hereinafter in connection with organic radicals or compounds respectively defines such with up to and including 7, preferably up and including 4 and advantageously one or two carbon atoms.

A lower alkyl group contains 1–7 carbon atoms, preferably 1–4 carbon atoms and represents for example ethyl, propyl, butyl or advantageously methyl.

A lower alkoxy group preferably contains 1–4 carbon atoms and represents for example methoxy, propoxy, isopropoxy or advantageously ethoxy. A mono-(lower-)alkylamino group preferably contains 1–4 carbon atoms in the alkyl portion and is for example N-methylamino, N-propylamino or advantageously N-ethylamino. A di-(lower)alkylamino group preferably contains 1–4 carbon atoms in each lower alkyl portion and represents, for example, N,N-dimethylamino, N-methyl-N-ethylamino and advantageously N,N-diethylamino.

Lower alkanoyloxy represents preferably acetoxy, propionoxy or pivaloyloxy.

Alkylenedioxy represents preferably ethylenedioxy, and advantageously methylenedioxy.

Aryl(lower)alkoxy represents advantageously e.g. benzyloxy, benzyloxy substituted by methyl, methoxy or chloro, and pyridylmethoxy.

Carboxy(lower)alkoxy represents advantageously e.g. 1-carboxyethoxy.

Lower alkoxycarbonyl(lower)alkoxy represents advantageously e.g. 1-(ethoxycarbonyl)ethoxy.

Amino(lower)alkoxy, mono-(lower)alkylamino(lower)alkoxy, di-(lower)alkylamino(lower)alkoxy advantageously represent respectively e.g. aminoethoxy, ethylaminoethoxy, diethylaminoethoxy.

Lower alkanoyloxymethoxy represents advantageously e.g. pivaloyloxymethoxy.

Bicycloalkyloxycarbonyl-(lower)alkoxy preferably represents bicyclo[2,2,1]heptyloxycarbonyl-(lower)alkoxy unsubstituted or substituted by lower alkyl, advantageously bornyloxycarbonylmethoxy.

Amino(lower)alkyl and ω-amino(lower)alkyl represent preferably amino(ethyl, propyl or butyl) and ω-amino(ethyl, propyl or butyl) respectively.

Halogen preferably represents chlorine, but may also be bromine, fluorine or iodine.

Acylated hydroxy represents preferably lower alkanoyloxy e.g. acetyloxy, benzoyloxy, benzoyloxy substituted on the phenyl ring by lower alkyl, halogen or lower alkoxy, e.g. methyl, chloro or methoxy respectively, or nicotinoyloxy.

Etherified hydroxy represents preferably lower alkoxy e.g. methoxy, or benzyloxy.

Aryloxy represents preferably phenoxy or phenoxy substituted by lower alkyl, lower alkoxy or halogen, e.g. methyl, methoxy or chloro respectively.

Arylthio represents preferably phenylthio or phenylthio substituted by lower alkyl, lower alkoxy or halogen, e.g. methyl, methoxy or chloro respectively.

Arylamino represents preferably anilino; aryl-N-(lower)alkylamino represents preferably N-methylanilino.

Acylamino-lower alkyl and ω-acylamino-lower alkyl represent preferably acylamino(ethyl, propyl or butyl) and ω-acylamino(ethyl, propyl or butyl) respectively.

Acylamino represents lower alkanoylamino, lower ~~carbonylamino~~, cycloalkylcarbonylamino, cycloalkyl(lower)alkox~~...~~ butyl or benzyl esters; the mono- or bis-amides, the mono- or di-N-alkylated amides, e.g. mono- or diethylamides; the mono or di-substituted lower alkyl esters, e.g. the ω-(amino, mono- or dimethylamino, carboxy or carbethoxy)-(ethyl, propyl or butyl) esters. Highly preferred functional derivatives are the mono esters, e.g. wherein one of $R_6$ and $R_7$ represents hydroxy and the other represents lower alkoxy.

Pharmaceutically acceptable salts are preferably metal or ammonium salts of said compounds of formula I wherein $R_o$ represents carboxy or of formula IA-IC wherein $COR_6$ and/or $COR_7$ represents carboxy, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)amines, lower alkylenediamines or lower hydroxyalkyl or aralkyl)alkylammonium bases, e.g., methylamine, diethylamine, triethylamine, dicyclohexylamine, triethanolamine, ethylenediamine, tris-(hydroxymethyl)aminomethane or benzyltrimethylammonium hydroxide. Said compounds of Formula I form acid addition salts, which are preferably such of therapeutically acceptable inorganic or organic acids, such as strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycolic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, benzenesulfonic, p-toluenesulfonic, naphthalenesulfonic, sulfanilic or cyclohexylsulfamic acid.

The compounds of formula I exhibit valuable pharmacological properties, e.g. cardiovascular effects, by inter alia inhibiting the release of Angiotensin II through selective inhibition of angiotensin-converting enzyme in mammals. The compounds are thus useful for treating diseases responsive to angiotensin-converting enzyme inhibition in mammals including man.

The compounds of this invention exhibit primarily hypotensive/antihypertensive and cardiac effects inter alia due to their angiotensin-converting enzyme inhibitory activity. These properties are demonstrable by in vivo or in vitro tests, using advantageously mammals, e.g., rats, cats, dogs or isolated organs thereof, as test ~~animals~~. The animals may either be normotensive or ~~hypertensive~~ e.g., genetically spontaneous hypertensive ~~o~~r renal hypertensive rats and dogs, and sodium-~~loade~~d dogs. The compounds can be applied to the ~~ani~~mals enterally or parenterally, advantageously ~~o~~r intravenously, for example within gelatin cap-~~sules~~ in the form of starchy suspensions or aqueous ~~solutions~~. The applied dosage may range between about ~~1 and~~ 100 mg/kg/day, preferably between about 0.05 ~~and 50 m~~g/kg/day, advantageously between about 0.1 ~~and 25 m~~g/kg/day.

~~The in~~ vivo lowering effect on the blood pressure is ~~recorded~~, either directly by means of a catheter, placed ~~in the te~~st animal's femoral artery, or indirectly by ~~tail~~ manometry at the rat's tail or a transducer. ~~The bloo~~d pressure is recorded in mm Hg prior to and ~~after dosi~~ng.

~~Th~~e antihypertensive effects are demonstrable in ~~spontaneou~~sly hypertensive rats by indirect measurement of systolic pressure. Conscious rats are placed individually in restraint cages within a gently warmed chamber. A rubber pulse sensor is placed distal to an inflatable occlusive cuff on each rat's tail. The cuff is periodically inflated to occlude the tail artery, and systolic pressure is recorded as the point where the first discernible pulse emerges along the decaying calibrated pressure curve. After obtaining control values of blood pressure and heart rate, test compounds are administered orally once daily for 4 consecutive days. Additional blood pressure measurements are usually made at 2.0, 4.0 and 23.5 hours after each daily dosing, and responses are compared to those of rats dosed with the treatment vehicle.

The compounds of this invention when administered intravenously or orally also exhibit an inbibitory effect against the Angiotensin I induced pressor response of normotensive rats. Angiotensin I is hydrolyzed by the action of said converting enzyme to the potent pressor substance Angiotensin II. The inhibition of said enzyme prevents the generation of Angiotensin II from I and, therefore, attenuates any pressor response following an Angiotensin I challenge.

The corresponding in vivo test is performed with male, normotensive rats, which are anesthetized with sodium 5-ethyl-5-(1-methylpropyl)-2-thiobarbiturate. A femoral artery and saphenous vein are cannulated respectively for direct blood pressure measurement and the i.v. administration of Angiotensin I and a compound of this invention. After the basal blood pressure is stabilized, pressor responses to 3 challenges of 333 ng/kg angiotensin I i.v., at 5 minute intervals, are obtained. Such pressure resonses are usually again obtained at 5, 10, 15, 30 and 60 minutes after i.v. administration or 1, 2, 3 and 4 hours after p.o. administration of the compound to be tested, and compared with the initial responses. Any observed decrease of said pressor response caused by the compounds of the invention is an indication of Angiotensin I converting enzyme inhibition.

The in vitro inhibition of the angiotensin-converting enzyme by the compounds of this invention can be demonstrated by a method analogous to that given in Biochim. Biophys. Acta 293, 451 (1973). According to this method, said compounds are dissolved at about 1 mM concentration in phosphate buffer. To 100 microliters of solutions of the test compound in phosphate buffer, diluted to the desired concentration, are added 100 microliters of 5 mM hippuryl-histidyl-leucine in phosphate buffer, followed by 50 microliters of the angiotensin-converting enzyme preparation (from lungs of adult male rabbits) in Tris buffer, containing potassium and magnesium chloride, as well as sucrose. Said solutions are incubated at 37° C. for 30 minutes and combined with 0.75 ml of 0.6N aqueous sodium hydroxide to stop further reaction. Then 100 microliters of a 0.2% solution of o-phthalaldehyde in methanol are added at room temperature, and 10 minutes later 100 microliters of 6N hydrochloric acid. These samples are read against water in a spectrophotometer set at 360 nm, and the optical densities thereof estimated. They are corrected for the standard curve via a conversion factor expressing nanomoles of histidyl-leucine formed during said 30 minute incubation period. The results are plotted against concentration to determine the IC$_{50}$, i.e., the concentration of the compound which gives half the activity of the control sample.

The aforementioned advantageous properties render the compounds of this invention of great value as specific therapeutic agents for mammals including man.

Accordingly, the compounds of this invention are valuable antihypertensive agents, especially useful for ameliorating hypertension (regardless of etiology) and/or cardiac conditions, such as congestive heart failure, and/or other edemic or ascitic diseases. They are also useful in the preparation of other valuable products, especially of corresponding pharmaceutical compositions.

The compounds of formula I according to the invention can be prepared in a manner which is known per se, in that, e.g.

(a) in a compound of the formula

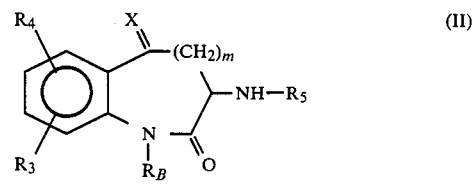

(II)

in which the carbocyclic ring may also be hexahydro and wherein X, $R_B$, $R_3$, $R_4$, $R_5$ and m have the meanings given hereinabove, $R_A$ is introduced by alkylation with a compound of the formula $$R_A-Z \qquad (IIIA)$$

wherein Z is a reactive esterified hydroxyl group and $R_A$ has the meanings given hereinabove or with a compound of the formula $$R_1-CO-R_o \qquad (IV)$$

wherein $R_1$ and $R_o$ have meanings given hereinabove, in the presence of a reducing agent with temporary protection of any primary and secondary amino groups and/or, optionally, hydroxyl and/or oxo groups, which may be present in any one of the residues X, $R_B$, $R_3$, $R_4$ and $R_5$, and/or in the alkylating agent, or (b) a compound of the formula

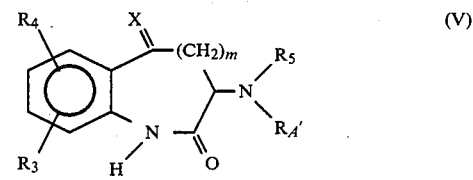

(V)

in which the carboxylic ring may also be hexahydro and wherein X, $R_3$, $R_4$, $R_5$ and m have the meanings given hereinabove and $R_A'$ is hydrogen or $R_A$ as defined hereinabove, is alkylated with a compound of the formula $$R_B-Z \quad (IIIB)$$

wherein Z is a reactive esterified hydroxyl group and $R_B$ has the meanings given hereinabove, while protecting temporarily any primary and secondary amino groups and/or, optionally, hydroxyl and/or oxo groups which may be present in any one of the residues X, $R_A$, $R_B$, $R_3$, $R_4$ and $R_5$, or (c) a compound of the formula

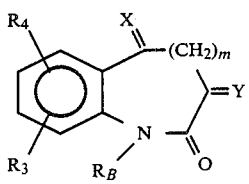

in which the carbocyclic ring may also be hexahydro and wherein Y is oxo or a reactive esterified hydroxyl group Z together with hydrogen, and X, $R_B$, $R_3$, $R_4$ and m have the meanings given hereinabove, is condensed with an amine of the formula $$R_A-NH-R_5 \qquad (VII)$$

wherein $R_A$ and $R_5$ have the meanings given hereinabove, with the proviso that when Y is oxo, the condensation is carried out in the presence of a reducing agent and with a temporary protection of the oxo group which may be present as the substituent X, or (d) in a compound of the formula

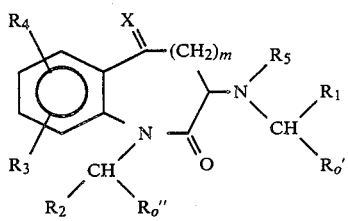

in which the carbocyclic ring may also be hexahydro and wherein X, $R_1$ to $R_5$ and m have the meanings given hereinabove, one of the symbols $R_o'$ and $R_o''$ is cyano and the other one is cyano or $R_o$ as defined hereinabove, the cyano group(s) is (are) subject to solvolysis, or (e) a compound of the formula

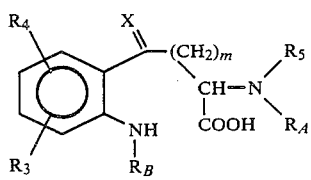

in which the carbocyclic ring may also be hexahydro or and wherein X, $R_A$, $R_B$, $R_3$, $R_4$, $R_5$ and m have the meanings given hereinabove, or an ester thereof, is cyclised, or (f) a compound which is structurally identical with a compound of formula I specified above, except for having an additional double bond located at C-3, or between the nitrogen atom and the adjacent carbon atom within the group $R_A$, is treated with a reducing agent in order to saturate this double bond, or (g) if desired, a resulting compound of formula I as specified above is converted into another compound of formula I within its above-specified scope, and/or (h) if desired, a resulting compound of formula I as specified above and having salt-forming properties is converted into a salt thereof or a free compound is liberated from such a salt, and/or (i) if desired, a resulting compound of formula I as specified above and having complex-forming properties is converted into a complex thereof, and/or (j) if so required, an optical isomer which has a specific configuration with respect to at least one center of chirality is enriched from a mixture of stereoisomeric forms of a resulting compound of formula I.

The alkylation according to processes (a) and (b), which serves for introduction of residues $R_A$ and $R_B$, respectively, is carried out in a conventional manner, advantageously by treating a corresponding starting material of formulae II and V, respectively, with an alkylating agent of the formula $R_A$—Z (IIIA) or $R_B$—Z (IIIB), respectively, wherein $R_A$ or $R_B$ have the meanings given hereinabove and Z is a reactive esterified hydroxyl group, such as a hydroxyl group esterified with a strong organic acid, e.g. an aliphatic or aromatic sulfonic acid (such as a lower alkanesulfonic acid, especially methanesulfonic, trifluoromethanesulfonic acid, especially benzenesulfonic, p-toluenesulfonic, p-bromobenzenesulfonic and p-nitrobenzenesulfonic acid) or with a strong inorganic acid, such as, especially, sulfuric acid, or a hydrohalic acid, such as hydrochloric or, most preferably, hydriodic or hydrobromic acid. The alkylation is carried out under conventional general conditions at temperatures ranging between about 0° C. up to the boiling temperature of the reaction mixture, preferably at temperatures between room temperature to about 100° C. The reaction takes place advantageously in the presence of a solvent which is inert with respect to the reactants, such as a chlorinated lower alkane (e.g. chloroform or methylene chloride), an acyclic or cyclic ether (e.g. diethyl ether, 1,2-dimethoxyethane, dioxane or tetrahydrofuran) and, in particular, a lower molecular weight tertiary amide (e.g. N,N-dimethylformamide, N,N-dimethylacetamide, N-methylpyrrolidone, N-ethylpiperidone and hexamethylphosphoric acid triamide). Advantageously, the strong acid HZ liberated during the reaction is bound by the addition of an acid-binding agent, such as, preferably, an inorganic acid-scavenger such as an alkali metal bicarbonate, carbonate or hydroxide, an organic quaternary ammonium salt (e.g. a tetrabutylammonium salt) or an organic tertiary base, such as triethylamine, N-ethylpiperidine, pyridine or quinoline.

In process (a), the alkylation can also be carried out under the conditions of reductive alkylation in the manner generally known and used in the art. In carrying out the alkylation, a compound of the general formula $$R_1-CO-R_o \qquad (IV)$$

in which $R_1$ and $R_o$ have the meanings given hereinabove, is reacted with the starting bicyclic compound II and, simultaneously or in a subsequent step, with a reducing agent. Among reducing agents which are used simultaneously with the alkylating agent, mention should be made of formic acid and complex metal hydrides such as sodium cyanoborohydride; among reducing agents used predominantly in a separate subsequent operation i.e. reduction of a preformed imine (Schiff's base), mention should be made of diborane and complex metal hydrides, such as, sodium borohydride, sodium cyanoborohydride which are added advantageously to the primary reaction mixture without isolating an intermediate, e.g. the imine. In this case, the alkylation is carried out advantageously in an organic solvent inert to the reducing agent, such as in an aliphatic or cyclic ether (such as diethyl ether, diisopropyl ether, 1,2-dimethoxyethane, dioxane or tetrahydrofuran) or an aliphatic alcohol (such as methanol, ethanol, isopropyl alcohol, glycol, glycol monomethyl ether or diethyleneglycol), preferably at about 0°–80° C. A principal reducing agent, however, which can be used both simultaneously and subsequently, is hydrogen, especially catalytically activated hydrogen. The catalysts are those conventionally used as hydrogenation catalysts, i.e. preferably those of the class of precious metals (such as palladium, platinum and rhodium) on a carrier (such as calcium carbonate, aluminum oxide or barium sulfate), in a finely dispersed suspension without carrier or, in form of complexes, in a homogeneous phase. Also, finely dispersed transition metals such as Raney metals, especially Raney nickel, are very suitable catalysts for the reductive alkylation. The specific reaction conditions depend, to a large extent, on the particular hydrogenation catalyst and its precise activity, and do not differ from those generally known for hydrogenation. Temperatures ranging from room temperature to about 150° C., and pressures of hydrogen ranging from atmospheric pressure to about 300 atmospheres are applicable according to the standard procedures of the art. In addition to the inert solvents which were mentioned above in connection with the hydride reduction, low molecular weight amides, especially tertiary amides (such as N,N-dimethylformamide, N,N-dimethylacetamide, N-methylpyrrolidone, N-ethylpiperidone, hexamethylphosphoric acid triamide), and also formamide and acetamide can be used as suitable solvents. Special measures have to be taken with starting materials of formula II which have an easily reducible functional group, such as the oxo group (X=O); in order to preserve these groups, selective reduction conditions, as known in the prior art, have to be applied, or, if a simultaneous reduction of these groups is desired or required, vigorous reagents and/or conditions are employed accordingly.

The preformed imines referred to above are preferably prepared by condensing an amine of formula II with a compound of formula IV in an inert solvent, e.g. toluene or methylene chloride, advantageously in the presence of a dehydrating catalyst, e.g. boron trifluoride etherate, p-toluenesulfonic acid or molecular sieves.

Process (b) is preferably carried out in the presence of very strong bases, such as alkali metal hydrides (e.g. sodium or potassium hydride), alkoxides (e.g. sodium methoxide or ethoxide, potassium tert-butoxide) or amides (e.g. lithium diisopropylamide), whereby ethers and amides mentioned above are preferred as solvents. In a special modification of process (b), starting materials are used in which $R_A'$ is hydrogen, and at least two equivalents of the reactant IIIB is employed. In the resulting product, both $R_A$ and $R_B$ are identical and within the scope of the meanings of $R_B$.

In any of the alkylation processes, primary and secondary amino groups in starting materials, except for the secondary amino group to be alkylated, must be in a temporarily protected form during the alkylation. Suitable protecting groups, as well as procedures for their introduction and removal are well known in the art, being elaborated in great detail in particular as general methods for the synthesis of peptides, cf. Houben-Weyl: Methoden der organishen Chemie; 4th edition, vol. 15/I and II, E. Wunsch (editor): Synthese von Peptiden (Georg Thieme Verlag, Stuttgart; 1974). The narrower selection of the protecting groups depends on the specific purpose, it being necessary to take into account in particular the specific properties of the particular starting materials and the reaction conditions of the specific process. In the case of several functional groups to be protected, advantageous combinations can be selected. Preferably, for example, similar or, even better, identical amino protecting groups, are used both in the radicals $R_o$ and in the radical $R_1$ and are simultaneously removed following alkylation.

Suitable as amino-protecting groups are especially amino-protecting groups that can be removed by reduction, for example especially those of the benzyloxycarbonyl type in which the benzyloxycarbonyl group may be substituted in the aromatic moiety by halogen atoms, lower alkoxy groups and/or lower alkyl radicals and, especially, by nitro groups, such as the p-chloro- and p-bromobenzyloxycarbonyl, p-methoxybenzyloxycarbonyl, p-methylbenzyloxycarbonyl and, especially, p-nitrobenzyloxycarbonyl group, or alternatively the isonicotinyloxycarbonyl group. An advantageous amino-protecting group is an ethoxycarbonyl group which carries in the β-position a silyl group substituted by three hydrocarbon radicals, such as triphenylsilyl, dimethyl-tert.-butylsilyl or, especially, trimethylsilyl. A β-(trihydrocarbylsilyl)-ethoxycarbonyl group of this type, such as a β-(tri-lower alkylsilyl)-ethoxycarbonyl group, for example, especially β-(trimethylsilyl)-ethoxycarbonyl, forms with the amino group to be protected a corresponding β-trihydrocarbylsilylethoxycarbonylamino group (for example the β-trimethylsilylethoxycarbonylamino group), which may be removed under very specific, very mild conditions by the action of fluoride ions.

It is also possible to use groups that can be removed by acidolysis, such as the tert-butoxycarbonyl groups and analogous groups, as well as those of the aralkyl type, such as benzhydryl, di-(4-methoxy)-benzhydryl and triphenylmethyl (trityl), or certain aralkoxycarbonyl groups of the 2-(p-biphenylyl)-2-propoxycarbonyl type, which are described in Swiss Patent Specification No. 509 266. It should be noted that protecting groups derived from esters of carbonic acids are in most cases also removable by basic hydrolysis.

For the optional temporary protection of hydroxy groups, protecting groups may be used advantageously that can be removed by reduction, cf. the above-cited text (Houben-Weyl), and also groups that can be removed by acidolysis, such as 2-tetrahydropyranyl, tert-butoxycarbonyl and tert-butyl. Preferred hydroxy-protecting groups that can be removed by reduction are, for example, benzyl groups that may be substituted in the aromatic moiety by halogen, lower alkyl, lower alkoxy and/or, especially, nitro, especially the 4-nitrobenzyl group. It is also possible to use acyl groups that can be removed under weakly basic conditions, such as formyl or trifluoroacetyl.

For the optional protection of oxo groups, these are preferably protected as ketals, especially as ketals derived from lower alkanols, such as methanol or ethanol, or advantageously of ethylene glycol, or as corresponding thioketals preferably those of 1,2-ethanedithiol. All these groups can liberate oxo groups under the conditions indicated further below.

The subsequent removal of protecting groups in accordance with the invention depends on their nature and is carried out in each case in a conventional manner known per se taking into consideration the general properties of the derived product. If the protecting groups for amino, hydroxy and oxo have been so selected that they can be removed under similar conditions (especially preferred here are the groups removable by acidolysis or, for amino and hydroxy, by reduction, that have already been given special mention), then all of these protecting groups are advantageously removed in a single operation; in special cases, however, it is possible to use different types of groups and remove each of them individually.

The groups that can be removed by reduction, especially those that contain halogenated lower alkyl radicals (for example 2,2,2-trichloroethyl radicals), isonicotinyl radicals (for example isonicotinyloxycarbonyl) and, especially, substituted benzyl radicals, especially 4-nitrobenzyl radicals of any kind, are preferably removed by zinc reduction, usually in the presence of an acid, preferably acetic acid, and with or without the addition of an inert organic solvent, usually at room temperature. The removal of a protecting group by acid hydrolysis (acidolysis) is carried out in the case of groups of the tert-butyl type by means of hydrogen chloride, hydrogen fluoride or trifluoroacetic acid, and in the case of acid-sensitive protecting groups chiefly by means of a lower aliphatic carboxylic acid, such as formic acid and/or acetic acid, in the presence of water and, optionally, a polyhalogenated lower alkanol or lower alkanone, such as 1,1,1,3,3,3-hexafluoropropan-2-ol or hexafluoroacetone. In this manner it is possible, for example, for an N-trityl group to be removed by an organic acid, such as formic acid, acetic acid, chloroacetic acid or trifluoroacetic acid, in aqueous or absolute trifluoroethanol as solvent (cf. German Offenlegungsschrift DT No. 2 346 147) or by aqueous acetic acid; for the tert-butoxycarbonyl group to be removed by trifluoroacetic acid or hydrochloric acid; and for the 2-(p-biphenylyl)-isopropoxycarbonyl group to be removed by aqueous acetic acid or, for example, by a mixture of glacial acetic acid, formic acid (82.8% strength) and water (7:1:2) or in accordance with the process in DT No. 2 346 147. The $\beta$-silylethyl ester groups are preferably removed by fluoride ion-yielding reagents, for example fluorides of quaternary organic bases, such as tetraethylammonium fluoride.

Ketalized and thioketalized oxo groups are converted into free oxo groups by acidolysis with usual strong inorganic acids, or with oxalic acid, in the presence of water, the latter ones advantageously by treatment with a sulfur-binding agent, e.g. a mercury II-salt and/or cadmium carbonate. Protecting groups that are unstable to basic conditions, for example formyl, trifluoroacetyl and carbonic acid ester groups, can be carefully removed by the action of an aqueous sodium or potassium bicarbonate or carbonate solution or, also, aqueous ammonia, in an organic solvent, usually at room temperature. The protecting groups are preferably removed under the reaction conditions of the examples, or under analogous conditions.

Those of the end products according to the invention that contain basic groups are obtained, depending on the manner of isolation, in the form of bases or acid addition salts; analogously, end products having acidic groups may also be obtained in the form of salts. Each form can be converted into the other in known manner. The bases can be obtained from the acid addition salts in a manner known per se. From the bases it is in turn possible to obtain acid addition salts, especially therapeutically useful acid addition salts, by reaction with acids, for example with acids of the type that form the above-mentioned salts. Acids and their salts also stand in a similar relationship to one another. Compounds that have both a free carboxy group and a basic group may be in the form of inner salts and these are obtained, for example, by establishing the isoelectric point.

The starting materials of formula IIIA, IIIB and IV, that is to say the alkylating agents, are known or, if they are unknown, can be simply obtained by conventional synthetic processes.

The starting materials of formula II and V can be obtained by conventional synthetic processes, and advantageously in the manner which is described in more detail and exemplified for specific intermediates hereinafter.

Process (c), also being an alkylation reaction is performed according to the same general consideration and under the same experimental conditions as the above processes (a) and (b) as described in detail above for the treatment with an alkylating agent of formula IIIA, IIIB or IV (i.e. substitutive alkylation or reductive alkylation). Starting materials of formula VI can be obtained by conventional processes known per se, e.g. in the manner described more specifically hereinafter. The amines of formula VII are known, or if unknown, they are easily accessible by conventional synthetic methods.

Process (d) is also carried out in a conventional manner under the general conditions of solvolysis, which are known to convert cyanides (nitriles) into free carboxylic acids or their salts, esters or amides. For conversion into a free acid, hydrolysis with water is carried out advantageously in an inert organic solvent which is at least partially miscible with water, such as an ether (e.g. diethyl or diisopropyl ether, 1,2-dimethoxyethane or, especially dioxane or tetrahydrofuran) or a lower alkanol (e.g. methanol, ethanol, isopropyl alcohol, a butyl alcohol, especially tert-butyl alcohol), a larger amount of water being required in the latter cases in order to prevent alcoholysis. The hydrolysis can be catalysed both by strong acids, especially inorganic acids such as sulfuric acid or, preferably hydrohalic acids (e.g. hydrobromic or, as a first choice, hydrochloric acid), or by bases, especially inorganic bases such as hydroxides and carbonates of alkali metals, e.g. sodium and potassium hydroxide. The bases are usually employed in at least stoichiometric quantities giving rise to carboxylic acid salts as primary products. The acidic catalysts are advantageously applied as dilute aqueous solution for the best result. Final products of formula I, in which $R_o$ represents an esterified carboxyl group, can be obtained by carrying out the solvolysis of the nitrile with the corresponding alcohol (alcoholysis) in the presence of a catalytic amount of an anhydrous strong acid, advantageously gaseous hydrogen chloride. Usually, excess alcohol is used as solvent; however, inert organic solvents can be added, such as acyclic and cyclic ethers (especially these mentioned above), and/or halogenated lower alkanes (especially chloroform and dichloromethane). If the alcoholysis is carried out under strictly anhydrous conditions, the primary product (imido ester) is to be hydrolyzed, advantageously by adding water to the reaction mixture; otherwise, by carrying out the alcoholysis in the presence of an approximately stoichiometric equivalent of water, the desired ester is obtained directly. In order to obtain a corresponding amide (i.e. a compound of formula I, wherein $R_o$ is carbamoyl), a corresponding nitrile of formula VIII can preferably be subjected to alkaline hydrolysis in the presence of hydrogen peroxide.

The starting materials of formula VIII can be obtained by conventional methods known per se, e.g. by a condensation analogous to that of process (c), in which a starting material of the above-defined formula VI is treated with an amine of the formula

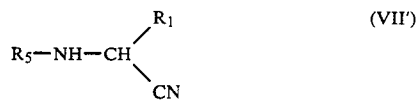

wherein $R_1$ and $R_5$ have the meanings given hereinabove, and which corresponds to the above-defined amine of formula VII. Also, processes (a) and (b) can analogously be used for the preparation of the nitriles of formula VIII.

The cyclization according to process variant (e) can also be carried out in the manner known per se, e.g. by dehydration. Especially useful general methods for this purpose are those developed in connection with the formation of the amide bond in peptides, as reviewed in compilative works, e.g. Houben-Weyl, Volumes 15/1 and 15/2 as cited hereinabove. According to one preferred modification, the amino group to be cyclized is rendered inactive by protonation (i.e. in the form of an acid addition salt), and the carboxyl group is converted into an activated ester, such as that with 2,4,5-trichlorophenol, pentachlorophenol, pentafluorophenol, 2-nitrophenol or, especially, 4-nitrophenol, or with an N-hydroxy compound, such as N-hydroxysuccinimide, 1-hydroxybenztriazole or N-hydroxypiperidine, or alternatively with an N,N'-disubstituted isourea, such as, especially, N,N'-dicyclohexylisourea, or a similar generally known activating agent. The cyclization is effected by basification preferably by the addition of an organic base, for example a quaternary ammonium salt, or especially a tertiary amine, such as triethylamine, N-ethylmorpholine or N-methylpiperidine, in order to reactivate the amino group to be cyclized by converting it into the unprotonated form. The reaction temperature is usually from $-20°$ to $+50°$ C., preferably approximately at room temperature, and customary solvents are used, for example, dioxan, tetrahydrofuran, acetonitrile, pyridine, dimethylformamide, dimethylacetamide, dimethylsulfoxide, N-methylpyrrolidone, hexamethylphosphoric acid triamide, as well as chloroform and methylene chloride, and expedient mixtures thereof. In a special variant of the process, the carboxy group can be directly activated in situ by the action of the free acid with a carbodiimide, such as N,N'-dicyclohexylcarbodiimide (optionally with the addition of N-hydroxysuccinimide, an unsubstituted or, for example, halogen-, methyl- or methoxy-substituted 1-hydroxybenztriazole or 4-hydroxybenzo-1,2-3-triazine-3-oxide or N-hydroxy-5-norbornene-2,3-dicarboximide), or with N,N'-carbonyldiimidazole.

Starting materials of formula IX can be obtained according to general methods known per se, e.g. as discussed in more specific examples hereinafter.

Also, reduction according to process (f) can be carried out in a manner generally known per se for saturation of such double bonds. More specifically, the double bond in the unsaturated starting materials corresponding to formula I can be located between C-3 and C-4 or between C-3 and the adjacent nitrogen atom, or between the nitrogen atom and the adjacent carbon atom within the group $R_4$. The saturation of the double bond is advantageously carried out by catalytic hydrogenation, e.g. under the preferred conditions discussed in detail hereinbefore, and also by metal reduction, such as zinc reduction in neutral or acidic medium, or, especially in the case of the C-N double bond, by diborane or complex hydrides such as sodium borohydride, as mentioned hereinbefore. The unsaturated starting materials for this process are obtained according to known general methods, e.g. those discussed in processes (a) and (c) and/or, in a more specific form hereinafter.

In performing the optical interconversions of a resulting final product of formula I, into another compound within the above-specified scope of formula I, transformations such as the following are carried out: an amino group is alkylated, and/or an oxo group, especially that of the symbol X, is converted into hydroxyl (plus hydrogen) or into two hydrogens by reduction and/or hydroxyl is converted into oxo by oxidation or into hydrogen by reduction, and/or a free hydroxyl or carboxyl group is liberated from its esterified form by hydrolysis or hydrogenolysis and/or a hydroxyl or amino group is acylated and/or a free carboxyl is esterified, and/or the aromatic carboxylic ring in formula I is hydrogenated to the hexahydro form, and/or the hexahydro carbocyclic ring is dehydrogenated to the aromatic carbocyclic ring.

All these optional interconversions are carried out by well-known conventional methods. A lower alkyl group as represented by $R_5$ can be introduced into the final product of formula I, wherein $R_5$ is hydrogen, by an alkylation reaction, using any of the modifications discussed in detail in connection with process (a). Both substitutive and reductive alkylation can be employed, the former with alkyl halides, the latter with lower aliphatic aldehydes and ketones and e.g. catalytically activated hydrogen or, in the case of formaldehyde, advantageously with formic acid as the reducing agent. By the substitutive alkylation, lower alkyl groups can also be introduced into a carbamoyl group represented by symbol $R_o$. Also, the reduction of the oxo group to hydroxy is carried out in the usual manner, e.g. by using a complex metal hydride, especially a mild reagent such as an alkali metal borohydride (e.g. sodium borohydride), or according to the method of Meerwein-Ponndorf, or a modification thereof using an alkanol, especially isopropyl alcohol, as both solvent and reducing agent and a metal alkoxide, preferably one corresponding to the reducing alcohol, such as aluminum isopropoxide, as a catalyst. The reduction of the oxo group to two hydrogens can advantageously be accomplished e.g. by treatment with amalgamated zinc and hydrochloric acid, or by Raney nickel desulfurization of a corresponding dithioketal. The oxidation of hydroxyl to oxo can be preferably carried out with a derivative of hexavalent chromium such as chromic acid or its salts, with a permanganate salt (especially potassium permanganate) or under the conditions of the Oppenauer oxidation, with acetone or cyclohexanone as oxidant and aluminum isopropoxide as catalyst. Esterified hydroxyl groups are liberated in particular by methods discussed in detail hereinabove in connection with removing hydroxyl-protecting groups; the acylation of both hydroxyl and amino groups is carried out in the usual way, preferably using a corresponding acid anhydride or halide. For esterification, a carboxyl group can be reacted directly with a diazoalkane, especially diazomethane, or with a corresponding alcohol in the presence of a strong acid catalyst (e.g. sulfuric acid or an organic sulfonic acid) and/or a dehydrating agent (e.g. dicyclohexylcarbodiimide) Alternatively, the carboxyl group can be converted into a reactive derivative thereof, such as an active ester mentioned in connection with process (e), or into a mixed anhydride, e.g. with an acid halide (i.e., especially an acid chloride), and this activated intermediate reacted with the desired alcohol.

The free carboxyl group can be liberated from an esterified carboxyl in a manner generally known, especially by base-catalyzed hydrolysis. Of special interest, however, are methods capable of selectively liberating one particular carboxyl group represented by the symbols —$COR_6$ and —$COR_7$. In such a case, use can be made of a proper combination of ester groups known in the art especially as carboxyl-protecting groups and developed in a great variety in particular for the synthesis of peptides, cf. Houben-Weyl, Volumes 15/1 and 15/2 as cited hereinabove. Radicals suitable for selective removal with liberation of the carboxyl are esters derived, for example, from alcohols that yield radicals that can be removed by acidolysis, such as cyanomethyl alcohol, benzoylmethyl alcohol or tert-butyl alcohol, but especially alcohols that yield radicals which can be removed by reduction, such as 2,2,2-trichloroethanol, benzyl alcohol, and especially 4-nitrobenzyl alcohol, or alternatively isonicotinyl alcohol. An especially advantageous class of substituted alkanols are ethyl alcohols which carry in the β-position a tri-substituted silyl group, such as triphenylsilyl, dimethyltert-butylsilyl or, especially, trimethylsilyl. As is described, for example, in Belgian Pat. No. 851,576, these alcohols are particularly suitable for selective removal because the corresponding β-silylethyl esters, for example β-(trimethylsilyl)-ethyl esters, have the stability of customary alkyl esters but can be selectively removed under mild conditions by the action of fluoride ions while retaining other esterified carboxyl groups, for example alkoxycarbonyl groups.

The removal of esterifying groups depends on their nature and is carried out in each case in a conventional manner known per se taking into consideration the properties of the other radicals involved. The groups that can be removed by reduction, especially those that contain halogenated lower alkyl radicals (for example 2,2,2-trichloroethyl radicals), isonicotinyl radicals (for example isonicotinyloxycarbonyl) and, optionally substituted benzyl radicals, especially 4-nitrobenzyl radicals of any kind, are preferably removed by zinc reduction, usually in the presence of an acid, preferably acetic acid, and with or without the addition of an inert organic solvent, usually at room temperature, those of the benzyl type, especially unsubstituted benzyl esters, also by hydrogenolysis techniques conventionally used for benzyl groups.

The removal of an ester group by acid hydrolysis (acidolysis) can be carried out especially in the case of groups of the tert-butyl type, by means of hydrogen chloride, hydrogen fluoride or trifluoroacetic acid. The β-silylethyl ester groups are preferably removed by fluoride-ion-yielding reagents, for example fluorides of quaternary organic bases, such as tetraethylammonium fluoride. Ester groups that are base-unstable can be carefully removed by the rapid action of an aqueous sodium or potassium bicarbonate solution or, preferably, aqueous ammonia in an organic solvent, usually at room temperature. The ester groups are preferably removed under the reaction conditions of the examples, or under analogous conditions.

A proper combination of the ester groups can be chosen in the earlier stages of the synthesis, or by a proper choice of starting materials and reactants, e.g. in process (a), a selectively removable ester group being introduced with a carboxyl which is to be liberated in the last stage.

The compounds of formula I in general, and IA in particular, are prepared advantageously according to reaction sequence 1, which involves an advantageous selection of starting materials and intermediates, in temporary protected form if required, comprises the following steps:

(a) condensing under conditions of basic catalysis, a compound of the formula

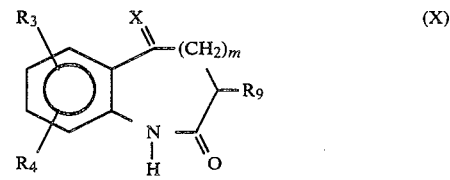

or a hexahydro derivative thereof wherein $R_3$, $R_4$ and X and m have meaning as previously defined; and $R_9$ is amino, lower alkylamino, azido or acylamino, e.g. lower alkanoylamino or alkyloxycarbonylamino with a compound of the formula

wherein $R_2$ and $R_7$ have meaning as previously defined; and Z represents reactively esterified hydroxy;

(b) optionally reducing, hydrogenolyzing, hydrolyzing or alkylating the resulting intermediate to obtain a compound of the formula II'

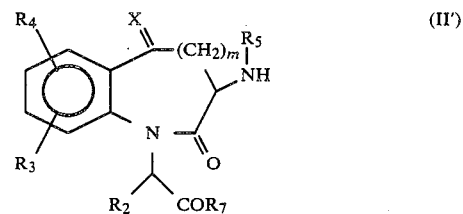

or a hexahydro derivative thereof wherein $R_2$ to $R_5$, $R_7$ and m are as defined above.

(c) condensing a compound of formula II' above or a hexahydro derivative thereof under conditions of reductive alkylation with a compound of the formula IV'

wherein $R_1$ and $R_6$ are as defined above; or condensing under alkylation conditions a compound of formula II' above or a hexahydro derivative thereof with a compound of the formula III'A

wherein $R_1$ and $R_6$ have meanings given above and Z represents reactively esterified hydroxy; and (d) optionally hydrolyzing or derivatizing the resulting product.

Compounds of formula X are obtained from the corresponding optionally substituted and/or derivatized 3,4,5,6-tetrahydro-1-benzazocin-2(1H)one or corresponding benzazonine derivative. These, in turn, are obtained from the corresponding cyclopent[b]-indole or 1,2,3,4-tetrahydrocarbazole by periodate oxidation (J. Chem. Soc. 1975, 1280; J. Amer. Chem. Soc. 88, 1049 (1966)); the keto-function may be reduced to the alcohol, e.g. with sodium borohydride or by catalytic hydrogenation. The alcohol function may be removed by conversion first to an ester, e.g. the O-acetyl derivative, or to an adduct with dicyclohexylcarbodiimide, followed by hydrogenolysis at elevated temperature and pressure.

Said tetrahydro-1-benzazocin-2(1H)-ones and hexahydrobenzazonin-2-ones are converted to the 3-halo-, e.g. the 3-bromo derivative, e.g. by treatment with phosphorus pentachloride followed by hydrogenation, or under conditions exemplified herein. Substitution of said halo derivative with a metal azide, e.g. sodium azide and subsequent reduction, or substitution with ammonia or a lower alkylamine and optional acylation, yields compounds of formula X.

Alternatively, compounds of formula X wherein $R_9$ represents amino, alkylamino or acylamino are obtained by reduction and cyclization of the appropriately substituted and/or derivatized (5 or 6)-o-nitrophenyl-2-amino-(pentanoic or hexanoic) acids and optional subsequent N-alkylation or N-acylation.

Compounds of formula X wherein $R_9$ is amino may be obtained from compounds of formula X wherein $R_9$ represents phthalimido, e.g. by reaction with hydrazine. Said phthalimido starting materials, e.g. for compounds wherein m=2, are obtained by cyclization of the 2-phthalimido-5-(o-aminophenyl)-pentanoic acid with e.g. dicyclohexylcarbodiimide or similar cyclization reagent well-known to the art. The 5-(o-aminophenyl)-2-phthalimidopentanoic acid or ester thereof is obtained e.g. by the palladium catalyzed coupling of 2-iodoaniline with N-phthalylallylglycine benzyl ester followed by hydrogenation.

Condensation of intermediates of formula II' with the known α-ketoacid derivatives of formula IV' (e.g. Chem. Ber. 31, 551, 3133) by reductive N-alkylation is carried out under conditions known to the art, e.g. by catalytic hydrogenation with hydrogen in the presence of platinum, palladium or nickel catalysts or with chemical reducing agents such as simple or complex light metal hydrides, advantageously an alkali metal cyanoborohydride such as sodium cyanoborohydride. The reductive amination with an alkali metal cyanoborohydride is preferably carried out in an inert solvent, e.g. methanol or acetonitrile, advantageously in the presence of an acid, e.g. hydrochloric acid or acetic acid at a temperature between about 0° and 50°, preferably room temperature.

Alkylation of intermediate amines of formula II' with a reactant of formula III'A, well known to the art, is carried out with or without basic catalysts such as triethylamine or potassium carbonate in an inert solvent.

The compounds of formula I in general, and IA in particular, can also be prepared by sequences 2 and 3.

Sequence 2 comprises the following steps:

(a) Condensing under conditions of reductive alkylation a compound of the formula XI

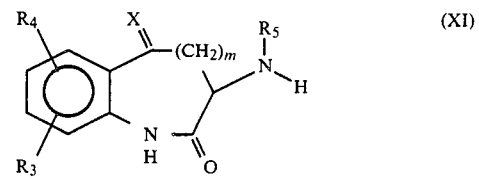

or a hexahydro derivative thereof wherein $R_3$, $R_4$, m and X have meanings as defined above; and $R_5$ is hydrogen or lower alkyl with a compound of the formula IV'

wherein $R_1$ and $R_6$ have meanings as previously defined, or under alkylation conditions with a compound of formula III'A

wherein $R_1$, $R_6$ and Z have meanings as previously defined to obtain a compound of the formula V'

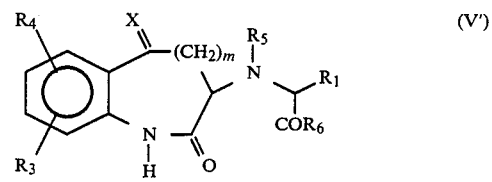

or a hexahydro derivatives thereof wherein $R_1$, $R_3$, $R_4$, $R_5$, $R_6$, X and m have meanings as previously defined.

(b) Condensing under conditions of basic catalysis a resulting compound of the formula V' with a compound of the formula III'B

wherein $R_2$ and $R_7$ and Z have meanings as previously defined; and (c) optionally hydrolyzing or derivatizing the resulting product;

Sequence 3 comprises the following steps:

(a) condensing a compound of the formula VII'

wherein $R_1$, $R_5$ and $R_6$ have meaning as defined above, with a compound of the formula VI'

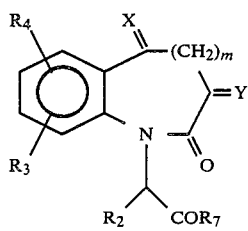

(VI')

or a hexahydro derivative thereof wherein $R_2$, $R_3$, $R_4$, $R_7$, m and X have meaning as defined above; and Y represents oxo or dichloro- under conditions of reductive N-alkylation, or condensing a compound of formula VII' with a compound of the above formula VI' wherein Y represents hydrogen and one reactive esterified or etherified hydroxy;

(b) optionally reducing, hydrolyzing or derivatizing the resulting product.

In the preceding sequences 2 and 3 the steps of lactam alkylation, reductive N-alkylation and alkylation of amines are advantageously carried out under the conditions described for process 1.

In sequences 1, 2 and 3 described herein, reactants of e.g. formulae III'A, III'B and VII' may be replaced with the corresponding nitriles, e.g. $R_2CH(Z)CN$, $R_1CH(Z)CN$ and $R_5NHCH(R_1)CN$ respectively. The nitriles thus obtained may be converted to the carboxylic acids, esters and amides of formula I using methods well known to the art.

The starting materials of formula VII or VII' represent amino acids and derivatives well known to the art or synthesized by methods well-known to the art. It is noteworthy that the optically active compounds of this invention may be synthesized starting with an optically active compound of formula VII or VII', e.g. L-α-aminophenylbutyric acid, L-phenylalanine, L-tryptophane, L-methionine, L-aspartic acid, L-threonine, L-glutamic acid, L-lysine, L-ornithine or derivatives thereof.

In the case of reactants of e.g. formulae III'A, III'B, IV' and VII' wherein $R_6$ or $R_7$ represent hydroxy, an appropriate carboxylate salt is prepared, preferably in situ, before condensation with the desired intermediates cited above.

Certain terms used in the foregoing processes have the meanings as defined below.

A reactively esterified hydroxy represents such esterified by a strong inorganic or organic acid, above all a hydrohalic acid, e.g. hydrochloric, hydrobromic or hydriodic acid, an aliphatic or aromatic sulfonic acid, e.g. methanesulfonic acid or p-toluenesulfonic acid.

Etherified hydroxy represents preferably lower alkoxy, e.g. methoxy, ethoxy or t-butoxy.

The optional steps of reducing, hydrogenolyzing, hydrolyzing or derivatizing the initial products of the aforesaid processes and the conversion of a resulting product into another compound of this invention are performed by chemical methodology known to the art and exemplified herein.

Compounds of formula I or IA wherein $R_6$ and/or $R_7$ is lower alkoxy may be amidized with ammonia, mono- or di-(lower)alkylamines to yield compounds of formula I or IA wherein $R_6$ and/or $R_7$ represents unsubstituted, mono- or di-(lower)alkylamino.

Conversion of compounds of formula I or IA wherein $R_6$ and/or $R_7$ is lower alkoxy, aryl(lower)alkoxy, amino, mono- or di-(lower alkyl)amino to compounds of formula I or IA wherein $R_6$ and/or $R_7$ represents hydroxy is advantageously carried out by hydrolysis with inorganic acids such as hydrohalic or sulfuric acid or with aqueous alkalies preferably alkali metal hydroxides such as lithium or sodium hydroxide.

The selective conversion of compounds of formula I or IA wherein $R_6$ and/or $R_7$ represents α-aryl(lower)alkoxy, e.g. benzyloxy to compounds of formula I or IA wherein $R_6$ and/or $R_7$ represents hydroxy is advantageously carried out by hydrogenolysis using hydrogen in the presence of a catalyst, e.g. palladium.

Compounds of formula I or IA wherein neither $R_6$ nor $R_7$ represents hydroxy may be converted to monocarboxylic acids of formula I or IA wherein one of $R_6$ and $R_7$ is hydroxy. Such conversion is carried out by selective hydrolytic or hydrogenolytic procedures well known to the art and based on the chemical character of the $R_6$ and $R_7$ substituents.

Free carboxylic acids of formula I or IA wherein $R_6$ and/or $R_7$ represent hydroxy or salts thereof may be esterified with the appropriate alcohols or reactive derivatives thereof well known to the art to give the corresponding mono- or bis-ester, namely compounds of formula I or IA wherein $R_6$ and/or $R_7$ is lower alkoxy, aryl(lower)alkoxy, lower alkanoyloxymethoxy, or lower alkoxycarbonyl)lower alkoxy. Furthermore the free carboxylic acids may be converted via reactive intermediates to mono- or bis-amides of formula I wherein $R_6$ and/or $R_7$ represents amino, mono- or di-(lower)alkylamino.

Compounds of formla I or IA, and intermediates therefor, wherein X represents oxo may be converted to the corresponding compounds wherein X represents one hydrogen and one hydroxy by reduction, e.g. by catalytic hydrogenation, e.g. with hydrogen in the presence of a platinum catalyst, or with a metal hydride reducing agent such as sodium borohydride. Resulting compounds wherein X represents one hydrogen and one hydroxy may be converted to compounds wherein X represents two hydrogens, e.g. by catalytic hydrogenation of the adduct of a carbodiimide, e.g. the adduct formed by condensation of a compound wherein X represents one hydrogen and one hydroxy with dicyclohexylcarbodiimide in the presence of cuprous chloride according to the general method described in Chem. Ber., 107, 1353 (1974).

Alternatively, the compounds wherein X represents one hydrogen and one hydroxy may be first converted to the corresponding compounds wherein X represents one hydrogen and one acylated hydroxy (or acyloxy e.g. acetoxy) and subsequently reduced, e.g. by catalytic hydrogenation in the presence of a palladium catalyst, to compounds wherein X represents two hydrogens.

Compounds of formula I or IA wherein $R_1$ represents amino (lower) alkyl may be converted to compounds wherein $R_1$ represents acylamino (lower) alkyl, or vice versa, by methods well-known in the art and described hereinabove in connection with protecting groups.

The above-mentioned reactions are carried out according to standard methods, in the presence or absence of diluents, preferably such as are inert to the reagents and are solvents thereof, of catalysts, condensing or said other agents respectively and/or atmospheres, at low temperatures, room temperature or elevated temperatures, preferably at the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially useful.

The invention also relates to novel starting materials and processes for their manufacture.

Depending on the choice of starting materials and methods, the new compounds may be in the form of one of the possible isomers or mixtures thereof, for example, depending on the number of asymmetric carbon atoms, as pure optical isomers, such as antipodes, or as mixtures of optical isomers such as racemates or mixtures of diastereoisomers.

Resulting mixtures of diastereoisomers and mixtures of racemates can be separated on the basis of the physicochemical differences of the constituents, in known manner, into the pure isomers, diastereoisomers or racemates, for example by chromatography and/or fractional crystallisation.

Resulting racemates can furthermore be resolved into the optical antipodes by known methods, for example by recrystallisation from an optically active solvent, by means of microorganisms or by reacting an acidic end product with an optically active base that forms salts with the racemic acid, and separating the salts obtained in this manner, for example on the basis of their different solubilities, into the diastereoisomers, from which the antipodes can be liberated by the action of suitable agents. Basic racemic products can likewise be resolved into the antipodes, for example, by separation of diastereomeric salts thereof, e.g. by the fractional crystallization of d- or l-tartrates. Any racemic intermediates or starting materials can likewise be resolved.

Advantageously, the more active of the two antipodes is isolated.

Finally, the compounds of the invention are either obtained in the free form, or as a salt thereof. Any resulting base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. A compound of formula I wherein $R_o$ represents carboxy or of formula IA wherein $COR_6$ and/or $COR_7$ represent carboxy can thus also be converted into the corresponding metal or ammonium salts. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for the crystallization.

The pharmaceutical compositions according to the invention are those suitable for enteral, such as oral or rectal, and parenteral administration to mammals, including man, for the treatment or prevention of diseases responsive to inhibition of angiotensin-converting enzyme, e.g. cardiovascular diseases such as hypertension and congestive heart failure comprising an effective amount of a pharmacologically active compound of formula I, or pharmaceutically acceptable salts thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starched, agar, alginic acid or its sodium salt, or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 kg may contain between about 10 to 200 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

In the case of compounds of formula I or IA wherein more than one asymmetric center exists the resulting diastereoisomeric compounds are denoted as A, B, etc., in the said examples. The respective diastereoisomeric compounds are characterized by physical properties, e.g. melting point, relative migration on chromatography, infrared, or nuclear magnetic resonance spectral properties.

In the case of compounds of formula I or IA wherein X is $H_2$ and an asymmetric center exists in the side chain at the carbon atom bearing the nitrogen atom, the symbols A and B have been assigned as follows to the respective isomers on the basis of their relative migration on chromatography. On the basis of migration on thin-layer chromatography and normal phase high pressure liquid chromatography employing silica gel as the stationary phase, the fast moving isomer is called isomer A and the slow moving isomer is called isomer B. On the basis of migration on reverse phase high pressure liquid chromatography the slow moving isomer is called isomer A and the fast moving isomer is called isomer B.

EXAMPLE 1

(a) A solution of 3-amino-1-ethoxycarbonylmethyl-3,4,5,6-tetrahydro-1-benzazocin-2-1H-one (1.0 g) in methanol (40 ml) and 10% aqueous sodium hydroxide (1.4 ml) is maintained at room temperature under a nitrogen atmosphere for 2 hours. The reaction mixture is evaporated to dryness under high vacuum to give the sodium salt of the aminoacid, mp 248°–250° (decomposition). This material, and ethyl benzylpyruvate (2.2 g) is dissolved in methanol/ethyl acetate (60:40; 60 ml). A solution of sodium cyanoborohydride (0.3 g) in methanol (10 ml) is added dropwise during 2 hours, and the reaction mixture is stirred at room temperature for 65 hours. Concentrated hydrochloric acid (2 ml) is added, and the mixture stirred for 1 hour. The solvents are removed under reduced pressure, water (50 ml) is added and the pH adjusted to 12 by the addition of 2N sodium hydroxide. The aqueous solution is extracted with ether (2×75 ml), then acidified (pH 4) concentrated hydrochloric acid and extracted with dichloromethane (2×100 ml). The combined dichloromethane solutions are dried over sodium sulfate and the solvent removed under reduced pressure to give a white foam. This material is dissolved in dichloromethane (25 ml) and hydrogen chloride bubbled in for 5 minutes. The solution is evaporated to dryness and boiled with ethyl acetate to give 1-carboxymethyl-3-(1-ethoxycarbonyl-3-phenylpropylamino)-3,4,5,6-tetrahydro-1-benzazocin-2-1H-one hydrochloride, m.p. 147°–149° dec.

(b) Subsequent treatment with dilute aqueous sodium hydroxide and methanol overnight at room temperature and subsequent acidification yields 1-carboxymethyl-3-(1-carboxy-3-phenylpropylamino)-3,4,5,6-tetrahydro-1-benzazocin-2-1H-one.

The starting material is prepared as follows:

DL-α-allylglycine (30 g) is added with stirring to a solution of anhydrous sodium carbonate (37.0 g) in water (1400 ml). N-Carbethoxyphthalimide (78.1 g) is added to the stirring solution, and stirring is maintained for an additional 30 minutes. The reaction mixture is filtered and made strongly basic by the addition of 2N sodium hydroxide. The solution is extracted with methylene chloride (4×500 ml) then acidified to pH 2 with 6N HCl. The solution is extracted with methylene chloride (4×500 ml), and the combined extracts dried over sodium sulfate. The solvent is removed under reduced pressure and the residue triturated with ether to give N-phthalylallylglycine, mp 107°–109° C., used without further purification in the next synthetic step.

The pH of a solution of N-phthalylallylglycine (45 g) in methanol (400 ml) and water (40 ml) is adjusted to 7.0 by the addition of 20% aqueous cesium carbonate. The solvents are removed under reduced pressure, and the residue dissolved in dimethylformamide (225 ml). The solution is evaporated under reduced pressure, then more dimethylformamide (225 ml) is added and evaporated. The residue is dissolved in dimethylformamide (360 ml) and benzyl bromide (35 g) is added, and the reaction mixture is stirred at room temperature for 65 hours. The solvent is removed under reduced pressure and the residue distributed between ethyl acetate (1000 ml) and water (500 ml). The organic phase is washed with 2N sodium hydroxide (200 ml), water (500 ml), and dried over sodium sulfate. The solvent is removed under reduced pressure and the residue triturated with ether to give N-phthalylallylglycine benzyl ester used without further purification in the next synthetic step.

A mixture of N-phthalylallylglycine benzyl ester (52.8 g), 2-iodoaniline (27.7 g), palladium (II) acetate (2.9 g), tri(o-tolyl)phosphine (7.75 g), triethylamine (22.2 ml), and acetonitrile (264 ml) is maintained at 100° C. in an autoclave under a nitrogen atmosphere for 18 hours. The solvent is removed under reduced pressure and the residue partitioned between water (500 ml) and methylene chloride (1500 ml). The aqueous phase is extracted with additional methlene chloride (500 ml), and the combined methylene chloride solutions dried over sodium sulfate. The solvent is removed under reduced pressure and the residue chromatographed on silica gel to give a principal fraction as an oil identified as benzyl 5-(2-aminophenyl)-2-phthalimido-4-pentenoate, which is used without further purification in the next synthetic step.

A solution of benzyl 5-(2-aminophenyl)-2-phthalimido-4-penteneoate (10.7 g) in ethanol (500 ml) is hydrogenated at atmospheric pressure with 10% palladium on charcoal (2 g) until uptake ceases. The catalyst is filtered off and the filtrate evaporated under reduced pressure. The residue is triturated with ethyl acetate to give 5-(2-aminophenyl)-2-phthalimidopentanoic acid, mp 258°–260°, used without further purification in the next synthetic step.

A solution of 5-(2-aminophenyl)-2-phthalimidopentanoic acid (3.5 g) and 1-(3-dimethylaminopropyl)-3-ethylcarbodiimide hydrochloride (1.9 g) in dimethylformamide (85 ml) is stirred at room temperature under a nitrogen atmosphere for 65 hours. The solvent is removed under high vacuum and the residue distributed between ethyl acetate (250 ml) and water (150 ml). The organic phase is washed with 2N sodium hydroxide (100 ml) and water (100 ml), and dried over sodium sulfate. The solvent is removed under reduced pressure and the residue recrystallized from methanol/ethyl acetate to give 3-phthalimido-3,4,5,6-tetrahydro-1-benzazocin-2-1H-one, mp 229°–230°, used without further purification in the next synthetic step.

A solution of 3-phthalimido-3,4,5,6-tetrahydro-1-benzazocin-2-1H-one (1.7 g) in dimethylformamide (10 ml) is stirred at 0° under a nitrogen atmosphere. A solution of potassium t-butoxide (0.75 g) in dimethylformamide (6 ml) is added and the reaction mixture is stirred at 0° for five minutes. A solution of ethyl bromoacetate (1.0 g) in dimethylformamide (5 ml) is added and the reaction mixture stirred at 0° for 1-½ hours. Water (3 ml) is added, and the reaction mixture is evaporated under high vacuum. The residue is distributed between ethyl acetae (100 ml) and water (50 ml) and the aqueous layer is washed with water (50 ml) and dried over sodium sulfate. The residue is recrystallized from methanol/ether to give 1-ethoxycarbonylmethyl-3-phthalimido-3,4,5,6-tetrahydro-1-benzazocin-2-1H-one, mp 79°–81° used in the next synthetic step.

A solution of 1-ethoxycarbonylmethyl-3-phthalimido-3,4,5,6-tetrahydro-1-benzazocin-2-1H-one (1.4 g) and hydrazine hydrate (0.19 g) in ethanol (400 ml) is refluxed for 4 hours. The solvent is removed under reduced pressure and the residue distributed between ethyl acetate (200 ml) and 2N hydrochlorid acid (125 ml). The organic phase is washed with 2N hydrochloric acid (100 ml). The combined hydrochloric acid solutions are made strongly basic with 2N sodium hydroxide, extracted with ethyl acetate (2×200 ml), and dried over sodium sulfate. The solvent is removed under reduced pressure and the residue recrystallized from ethanol/ether to give 3-amino-1-ethoxycarbonylmethyl-3,4,5,6-tetrahydro-1-benzazocin-2-1H-one as an oil, used without further purification in the next synthetic step.

3-Phthalimido-3,4,5,6-tetrahydro-1-benzazocin-2-1H-one may also be prepared as follows.

A solution of 6-acetoxy-3,4,5,6-tetrahydro-1-benzazocin-2-1H-one (7.4 g) in ethanol (250 ml) is hydrogenated at 3 atmosphere at 70° using 10% palladium on charcoal (1.5 g) as catalyst. The catalyst is filtered off and the solvent removed under reduced pressure. The residue is recrystallized from methanol/ethyl acetate to give 3,4,5,6-tetrahydro-1-benzazocin-2-1H-one.

To a solution of 4.7 g of 3,4,5,6-tetrahydro-1-benzazocin-2-1H-one, [J. Chem. Soc. (C), 2716 (1969)] in chloroform (75 ml), phosphorus pentachloride (5.9 g) is added in portions, while maintaining the temperaure at 0°-5°. When addition is complete, iodine (60 mg) is added, followed by bromine (4.5 g), which is added dropwise over five minutes. The mixture is then refluxed for 4 hours. The chloroform solution is evaporated and the residue partitioned between ice/water (60 ml) and dichloromethane (100 ml). The organic phase is dried over magnesium sulfate and evaporated under reduced pressure. The crude residue is purified by chromatography on silica gel, eluting with ether/hexane mixtures. Concentration of the appropriate fractions yields 3-bromo-3,4,5,6-tetrahydro-1-benzazocin-2-1H-one.

A solution of 3-bromo-3,4,5,6-tetrahydro-1-benzazocin-2-1H-one (3.0 g) and potassium phthalimide (2.3 g) in dimethylformamide (150 ml) is maintained at 90° for 18 hours. The reaction mixture is cooled to room temperature and poured into water (450 ml). Stirring is maintained for 2 hours and 3-phthalimido-3,4,5,6-tetrahydro-1-benzazocin-2-1H-one is filtered off and dried.

EXAMPLE 2

A solution of 3-amino-1-carboxymethyl-1,3,4,5,6,7-hexahydro-1-benzazonin-2-one sodium salt (13.2 g) and ethyl benzylpyruvate (30 g) in acetic acid (100 ml) and methanol (75 ml) is stirred at room temperature under an atmosphere of dry nitrogen for one hour. A solution of sodium cyanoborohydride (3.5 g) in methanol (30 ml) is then added dropwise during 4 hours. The reaction mixture is stirred at room temperature for 18 hours. Concentrated hydrochloric acid (10 ml) is added dropwise and the reaction mixture stirred at room temperature for 1 hour. The solvents are removed under reduced pressure and the residue partitioned between water (400 ml) and ether (100 ml). The pH is adjusted to 9 by the addition of 40% aqueous sodium hydroxide, and the ether layer is discarded. The pH of the aqueous phase is adjusted to 4.3 by the addition of concentrated hydrochloric acid, and the solution is extracted with ethyl acetate (3×100 ml).

The ethyl acetate extracts are combined and dried over magnesium sulfate and the solvent removed under reduced pressure. The residue is dissolved in dichloromethane (150 ml) and hydrogen chloride gas is bubbled in for five minutes. The solvent is evaporated and the residue is recrystallized to give 1-carboxymethyl-3-(1-ethoxycarbonyl-3-phenylpropylamino)-1,3,4,5,6,7-hexahydro-1-benzazonin-2-one.

The starting material is prepared as follows:

A solution of 3,4,5,6-tetrahydro-1H-1-benzazonin-2,7-dione (14.2 g), J. Am. Chem. Soc. 88, 1049 (1966), and sodium borohydride (1.4 g) in ethanol (720 ml) is stirred at room temperature for 18 hours. The ethanol is removed under reduced pressure, and the residue dissolved in dichloromethane (350 ml). The solution is extracted with 2N hydrochloric acid (2×200 ml) and saturated brine (100 ml), and dried over sodium sulfate. The solvent is removed under reduced pressure to give 7-hydroxy-1,3,4,5,6,7-hexahydro-1-benzazonin-2-one.

A solution of 7-hydroxy-1,3,4,5,6,7-hexahydro-1-benzazonin-2-one (9.2 g) in acetic anhydride (200 ml) is maintainwed at 80° for 3 hours. The reaction mixture is cooled to room temperature and the solvents removed under reduced pressure. Ether (300 ml) is added, and the resulting solution washed with water (150 ml) and dried over magnesium sulfate. The solvent is removed under reduced pressure to give 7-acetoxy-1,3,4,5,6,7-hexahydro-1-benzazonin-2-one.

A solution of 7-acetoxy-1,3,4,5,6,7-hexahydro-1-benzazonin-2-one (7.4 g) in ethanol (250 ml) is hydrogenated at 3 atmospheres at 70° using 10% palladium on charcoal (1.5 g) as catalyst. The catalyst is filtered off and the solvent removed under reduced pressure. The residue is recrystallized to give 1,3,4,5,6,7-hexahydro-1-benzazonin-2-one.

To a solution of 1,3,4,5,6,7-hexahydro-1-benzazonin-2-one (4.7 g) in chloroform (75 ml), phosphorus pentachloride (5.9 g) is added in portions, while maintaining the temperature at 0°-5°. When addition is complete, iodine (60 mg) is added, followed by bromine (4.5 g), which is added dropwise over five minutes. The mixture is then refluxed for 4 hours. The chloroform solution is evaporated and the residue partitioned between ice/water (60 ml) and dichloromethane (100 ml). The organic phase is dried over magnesium sulfate and evaporated under reduced pressure. The crude residue is purified by chromatography on silica gel, eluting with ether/hexane mixtures. Concentration of the appropriate fractions yields 3-bromo-1,3,4,5,6,7-hexahydro-1-benzazonin-2-one.

A solution of 3-bromo-1,3,4,5,6,7-hexahydro-1-benzazonin-2-one (14.2 g) and sodium azide (7.1 g) in dimethylsulfoxide (400 ml) is maintained at 80° under an atmosphere of nitrogen for 3 hours. The reaction mixture is poured into ice/water (1200 ml) and the suspension is stirred for 30 minutes. The solid is filtered off, washed with water (300 ml) and dried to give 3-azido-1,3,4,5,6,7-hexahydro-1-benzazonin-2-one.

A solution of 3-azido-1,3,4,5,6,7-hexahydro-1-benzazonin-2-one (8.9 g) in dry dimethylformamide (100 ml) is added during 30 minutes to a solution of potassium t-butoxide (4.5 g) in dry dimethylformamide (100 ml) maintained at 0° under an atmosphere of dry nitrogen. The reaction mixture is stirred at 0° for 2 hours, when a solution of ethyl bromoacetate (5.8 g) in dimethylformamide (10 ml) is added during 5 minutes. The reaction mixture is stirred at 0° for 2 hours, then evaporated under reduced pressure. The residue is distributed between ethyl acetate (250 ml) and water (150 ml), and the ethyl acetate solution washed with water (100 ml) and dried over sodium sulfate. The solvent is removed under reduced pressure to give 3-azido-1-ethoxycarbonylmethyl-1,3,4,5,6,7-hexahydro-1-benzazonin-2-one.

A solution of 3-azido-1-ethoxycarbonylmethyl-1,3,4,5,6,7-hexahydro-1-benzazonin-2one (5.0 g) in ethanol (500 ml) is hydrogenated at atmospheric pressure using 10% palladium on charcoal (0.7 g) as catalyst. The catalyst is filered off and the solvent removed under reduced pressure to give 3-amino-1-ethoxycarbonylmethyl-1,3,4,5,6,7-hexahydro-1-benzazonin-2-one.

A solution of sodium hydroxide (2.0 g) in water (5 ml) is added to a solution of 3-amino-1-ethoxycarbonylmethyl-1,3,4,5,6,7-hexahydro-1-benzazonin-2-one (15.0 g) is methanol (150 ml) at room temperature, and the solution is stirred for two hours. The solvents are evaporated and the residue thoroughly dried to give 3-amino-1-carboxymethyl-1,3,4,5,6,7-hexahydro-1-benzazonin-2-one sodium salt.

EXAMPLE 3

According to procedures illustrated in the previous examples, 6-acetoxy-3,4,5,6-tetrahydro-1-benzazocin-2-1H-one is converted to 6-acetoxy-1-carboxymethyl-3-(1-ethoxycarbonyl-3-phenylpropylamino)-3,4,5,6-tetrahydro-1-benzazocin-2-1H-one.

The starting material is prepared as follows:

A solution of 4,5-dihydro-1-benzazocin-2,6-1H,3H-dione (14.2 g) [Tetrahedron Letters 4079–4082 (1976)] and sodium borohydride (1.4 g) in ethanol (720 ml) is stirred at room temperature for 18 hours. The ethanol is removed under reduced pressure, and the residue dissolved in dichloromethane (350 ml). The solution is extracted with 2N hydrochloric acid (2×200 ml) and saturated brine (100 ml), and dried over sodium sulfate. The solvent is removed under reduced pressure to give 6-hydroxy-3,4,5,6-tetrahydro-1-benzazocin-2-1H-one.

A solution of 6-hydroxy-3,4,5,6-tetrahydro-1-benzazocin-2-1H-one (9.2 g) in acetic anhydride (200 ml) is maintained at 80° for 3 hours. The reaction mixture is cooled to room temperature and the solvents removed under reduced pressure. Ether (300 ml) is added, and the resulting solution washed with water (150 ml) and dried over magnesium sulfate. The solvent is removed under reduced pressure to give 6-acetoxy-3,4,5,6-tetrahydro-1-benzazocin-2-1H-one.

EXAMPLE 4

(a) A solution of 3-[(5-benzyloxycarbonylamino-1-(S)-methoxycarbonylpentyl)amino]-1-ethoxycarbonylmethyl-3,4,5,6-tetrahydro-1-benzazocin-2-1H-one (isomer B) (3.2 g) in methanol (20 ml) is added to a solution of sodium hydroxide (1.0 g) in water (3 ml). The reaction mixture is stirred at room temperature for 2 hours then acidified by the addition of 2N hydrochloric acid.

The solution is evaporated under reduced pressure to give 3-[(5-benzyloxycarbonylamino-1-(S)-carboxypentyl)amino]-1-carboxymethyl-3,4,5,6-tetrahydro-1-benzazocin-2-1H-one (isomer B).

(b) A solution of 3-[(5-benzyloxycarbonylamino-1-(S)-methoxycarbonylpentyl)amino]-1-ethoxycarbonylmethyl-3,4,5,6-tetrahydro-1-benzazocin-2-1H-one (isomer A) (2.6 g) in methanol (15 ml) is added to a solution of sodium hydroxide (0.8 g) in water (2.5 ml). The reaction mixture is stirred at room temperature for 2 hours then acidified by the addition of 2N hydrochlorid acid. The solution is evaporated under reduced pressure to give 3-[(5-benzyloxycarbonylamino-1-(S)-carboxypentyl)amino]-1-carboxymethyl-3,4,5,6-tetrahydro-1-benzazocin-2-1H-one (isomer A).

The starting materials may be prepared as follows:

A solution of 3-amino-1-ethoxycarbonylmethyl-3,4,5,6-tetrahydro-1-benzazocin-2-1H-one (8.0 g), acetic acid (0.4 ml), and t-butyl nitrite (4.2 ml) is dissolved in chloroform (150 ml) and the solution is refluxed for 2 hours then cooled to room temperature. m-Chloroperbenzoic acid (5.7 g) is added in portions, and the resulting solution stirred at room temperature for 30 minutes. The solution is washed with saturated aqueous sodium bicarbonate (120 ml), water (75 ml), 2N hydrochloric acid (50 ml), water (50 ml), 2N hydrochloric acid (50 ml), and water (50 ml). The solution is dried over magnesium sulfate and the solvent removed under reduced pressure to give 1-ethoxycarbonylmethyl-5,6-dihydro-1-benzazocin-2,3-1H,4H-dione.

A solution of 1-ethoxycarbonylmethyl-5,6-dihydro-1-benzazocin-2,3-1H,4H-dione (4.2 g), ε-benzyloxycarbonyllysine methyl ester (4.8 g), and dibutyltin dichloride (0.32 g) in dichloromethane (100 ml) is stirred with 4 Å molecular sieves (45 g) under reflux for 48 hours. The reaction mixture is cooled to room temperature, filtered, and the solvent removed under reduced pressure to give a product which is dissolved in methanol (100 ml) and acetic acid (5 ml). Sodium cyanoborohydride (0.36 g) is added after 10 minutes and the reaction mixture stirred at room temperature for 65 hours. The reaction mixture is acidified with concentrated hydrochloric acid and evaporated under reduced pressure. The residue is partitioned between ethyl acetate (150 ml) and 2N hydrochloric acid, and the aqueous layer basified and extracted with dichloromethane (2×100 ml). The solution is dried over magnesium sulfate and evaporated under reduced pressure to give an oil which is separated into two discrete fractions (isomer A and isomer B of 3-[(5-benzyloxycarbonylamino-1-(S)-methoxycarbonylpentyl)-amino]-1-ethoxycarbonylmethyl-3,4,5,6-tetrahydro-1-benzazocin-2-1H-one.

EXAMPLE 5

(a) A solution of 3-[(5-benzyloxycarbonylamino-1-(S)-carboxypentyl)amino]-1-carboxymethyl-3,4,5,6-tetrahydro-1-benzazocin-2-1H-one (isomer B) (2.1 g) in ethanol (300 ml) is hydrogenated at atmospheric pressure using 5% palladium on charcoal (0.5 g) as catalyst. The catalyst is filtered off and the solvent is removed under reduced pressure to give 3-[(5-amino-1-(S)-carboxypentyl)amino]-1-carboxymethyl-3,4,5,6-tetrahydro-1-benzazocin-2-1H-one (isomer B).

(b) Similarly, 3-[(5-benzyloxycarbonylamino-1-(S)-carboxypentyl)amino]-1-carboxymethyl-3,4,5,6-tetrahydro-1-benzazocin-2-1H-one (isomer A) is hydrogenated to give 3-[(5-amino-1-(S)-carboxypentyl)amino]-1-carboxymethyl-3,4,5,6-tetrahydro-1-benzazocin-2-1H-one (isomer A).

EXAMPLE 6

According to the procedures described in the previous examples the following compounds of formula Ia and derivatives wherein $R^2$ and $R^5$=H, X=2 hydrogens, $R^6$=hydroxy or ethoxy, $R^7$=hydroxy, m=2 or 3, advantageously as the S,S isomers, may be prepared.

| Compounds | $R^3$ | $R^4$ | $R^1$ | m | derivative |
|---|---|---|---|---|---|
| 6a | OCH$_3$ | OCH$_3$ | CH$_2$CH$_2$C$_6$H$_5$ | 3 | — |
| 6b | H | H | (CH$_2$)$_3$NHCOOCH$_2$C$_6$H$_5$ | 2,3 | — |
| 6c | H | H | (CH$_2$)$_4$NHCOOCH$_2$C$_6$H$_5$ | 3 | — |
| 6d | H | H | CH$_2$CH$_2$C$_6$H$_5$ | 2,3 | hexahydro |
| 6e | H | Cl | CH$_2$CH$_2$C$_6$H$_5$ | 2 | — |
| 6f | H | H | CH$_2$COOEt | 2,3 | — |
| 6g | H | H | n-propyl | 2,3 | — |
| 6h | H | H | (CH$_2$)$_4$NHCOOCH$_2$C$_6$H$_5$ | 2,3 | hexahydro |
| 6i | H | H | phenoxyethyl | 2,3 | — |

-continued

| Compounds | R³ | R⁴ | R¹ | m | derivative |
|---|---|---|---|---|---|
| 6j | H | H | phenylthioethyl | 2,3 | — |

Starting materials for
6a - reported in J. Chem. Soc. Perkin II, 733 (1978)
6b - L-ornithine
6c - L-lysine
6d - 6h-3-amino-1-carboxymethyl-3,4,5,6-tetrahydro-1-benzazocin-2-1H—one is hydrogenated with ruthenium on alumina catalyst in glacial acetic acid at 120° and 100 atmospheres pressure to give 3-amino-1-carboxymethylperhydro-1-benzazocin-2-one; 3-amino-1-carboxymethyl-perhydrobenzazonin-2-one can be similarly prepared.
6e - reported in J. Chem. Soc. (C), 2176 (1969)
6f - L-aspartic acid
6g - ethyl 2-oxopentanoate
6i - ethyl 4-phenoxy-2-aminobutyrate
6j - ethyl 4-phenylthio-2-aminobutyrate

EXAMPLE 7

(a) To 1-ethoxycarbonylmethyl-3-(1-ethoxycarbonyl-3-phenyl-(1S)-propylamino)-3,4,5,6-tetrahydro-(3S)-1-benzazocin-2-1H-one (0.56 g) in 40 ml of methanol at room temperature is added a solution of sodium hydroxide (0.11 g) in 5 ml of water. The reaction is stirred at room temperature for 2 hours. The reaction mixture is evaporated, dissolved in 5 ml of water and washed with 2×50 ml of diethyl ether. The aqueous layer is adjusted to pH 2 with 6N hydrochloric acid, producing a precipitate. The solid is collected by filtration and dried in vacuo at 50° to give 1-carboxymethyl-3-(1-carboxy-3-phenyl-(1S)-propylamino)-3,4,5,6-tetrahydro-(3S)-1-benzazocin-2-1H-one hydrochloride, mp. 148°-150°, $\alpha_D = -24°$ (c=1.0, methanol).

(b) Starting with 1-ethoxycarbonylmethyl-3-(1-ethoxycarbonyl-3-phenyl-(1S)-propylamino)-3,4,5,6-tetrahydro-(3R)-1-benzazocin-2-1H-one (1.0 g) in 50 ml of methanol and sodium hydroxide in 5 ml water, the procedure described above is followed to give 1-carboxymethyl-3-(1-carboxy-3-phenyl-(1S)-propylamino)-3,4,5,6-tetrahydro-(3R)-1-benzazocin-2-1H-one hydrochloride, mp. 169°-171°, $\alpha_D = +104°$ (c=1.0, methanol).

The starting materials are prepared as follows:

To 3,4,5,6-tetrahydro-1-benzazocin-2-1H-one (12.0 g), prepared as described by R. Huisgen and L. Krause in Ann. Chem., 574, 171 (1951), in 150 ml of chloroform at 0° is added phosphorous pentachloride (15.0 g) followed by iodine (0.15 g). The reaction is stirred for 30 minutes and then bromine (12.0 g) is added in 5 minutes. The reaction is refluxed 4 hours, cooled to room temperature, and poured into an ice-water mixture. The chloroform layer is washed with 50 ml of water, dried over magnesium sulfate and evaporated to give 3-bromo-3,4,5,6-tetrahydro-1-benzazocin-2-1H-one, homogeneous by silica gel thin layer chromatography ($R_f$=0.6 in 1:1 ethyl acetate-toluene), NMR (CDCl₃) 8.56 (1H, broad), 6.69-7.94 (4H, m), 4.34 (1H, t), 1.02-3.33 (6H, m); MS (m/e) 253.

The above bromide (1.0 g) and sodium azide (0.30 g) in 20 ml of dimethylsulfoxide are stirred for 5 hours at 60°. The reaction is poured into 125 ml of cold water to give a solid, which is collected by filtration and dried in vacuo at 60° to give 3-azido-3,4,5,6-tetrahydro-1-benzazocin-2-1H-one, IR (Nujol) 2110, 1650 cm⁻¹; NMR (DMSO-d₆) 10.2 (1H, broad), 7.02-7.61 (4H, m), 3.36 (1H, m), 1.18-2.95 (6H, m); MS (m/e) 188 (M-28), 187, 132.

To the above azide (5.0 g) in 250 ml of tetrahydrofurane at room temperature is added potassium t-butoxide (2.9 g). After the reaction stirred for 1 hour, ethyl bromoacetate (4.3 g) in 10 ml of tetrahydrofurane is added. The reaction is stirred for 36 hours at room temperature and then evaporated. The residue in 50 ml of water is extracted with 3×50 ml of methylene chloride. The organic portions are dried over magnesium sulfate and evaporated to give 1-ethoxycarbonylmethyl-3-oxo-3,4,5,6-tetrahydro-1-benzazocin-2-1H-one, IR (CHCl₃) 1640, 1720, 1750 cm⁻¹; MS (m/e) 274, 247, 202, 174.

The above ketone (2.75 g) and ethyl 2-amino-4-phenyl-(2S)-butyrate (2.1 g) in 200 ml of chloroform containing di-n-butyltin dichloride (0.15 g) are refluxed using a water separator for 24 hours. The reaction mixture is evaporated to give a crude imine which is used directly.

To the above imine (4.6 g) in 75 ml of methanol and 15 ml of acetic acid is added sodium cyanoborohydride (0.85 g). The reaction is stirred for 20 hours at room temperature. 2.5 ml of 12N hydrochloric acid are added and the reaction mixture is evaporated. The residue in 50 ml of 10% aqueous sodium carbonate is extracted with 3×75 ml of methylene chloride. The combined organic portions are dried over magnesium sulfate and evaporated to give an oil. The diastereomeric amines are separated by flash column chromatography (silica gel, 3:1 toluene-ethyl acetate) to give 1-ethoxycarbonyl-methyl-3-(1-ethoxycarbonyl-3-phenyl-(1S)-propylamino)-3,4,5,6-tetrahydro-(3R)-1-benzazocin-2-1H-one, $R_f$=0.5 in 1:1 ethyl acetate-toluene, NMR (CDCl₃) 6.93-7.42 (9H, m), 4.41 (2H, s), 4.13 (4H, q, J=7), 1.22 (3H, t, J=7) and 1-ethoxycarbonylmethyl-3-(1-ethoxycarbonyl-3-phenyl-(1S)-propylamino)-3,4,5,6-tetrahydro-(3S)-1-benzazocin-2-1H-one, $R_f$=0.48 in 1:1 ethyl acetate-toluene, NMR (CDCl₃), 7.24 (9H, m), 4.44 (2H, s), 4.19 (4H, q, J=7), 1,26 (3H, t, J=7),1.02 (3H, t, J=7).

EXAMPLE 8

(a) 1-Benzyloxycarbonylmethyl-3-(1-ethoxycarbonyl-3-phenyl-(1S)-propylamino)-3,4,5,6-tetrahydro-(3S)-1-benzazocin-2-1H-one (1.0 g) in 150 ml of ethanol is hydrogenated at one atmosphere pressure in the presence of 0.5 g of 10% palladium on carbon. The reaction mixture is filtered and evaporated, HCl gas is bubbled through a solution of the residue in 100 ml of diethyl ether. The product is collected by filtration to give 1-carboxymethyl-3-(1-ethoxycarbonyl-3-phenyl-(1S)-propylamino-3,4,5,6-tetrahydro-(3S)-1-benzazocin-2-1H-one hydrochloride, mp. 96°-98°, $\alpha_D = -15°$ (c=1.0 in methanol).

(b) Starting with 1-benzyloxycarbonylmethyl-3-(1-ethoxycarbonyl-3-phenyl-(1S)-propylamino-3,4,5,6-tetrahydro-(3R)-1-benzazocin-2-1H-one (2.2 g), the procedure described above is used to give 1-carboxymethyl-3-(1-ethoxycarbonyl-3-phenyl-(1S)-propylamino)-3,4,5,6-tetrahydro-(3R)-1-benzazocin-2-1H-one hydrochloride.

The starting materials are prepared as follows:

To 3-azido-3,4,5,6-tetrahydro-1-benzazocin-2-1H-one (4.0 g) in 250 ml of tetrahydrofurane is added potassium t-butoxide (2.3 g). After the reaction has stirred 1 hour at room temperature, benzyl bromoacetate (4.7 g) in 10 ml of tetrahydrofurane is added. The reaction is stirred for 36 hours at room temperature and then evaporated. The residue in 50 ml of water is extracted with 3×50 ml of methylene chloride. The organic portions are dried over magnesium sulfate and evaporated to give 1-benzyloxycarbonylmethyl-3-oxo-3,4,5,6-tetrahydro-1-benzazocin-2-1H-one, IR (Neat) 1660, 1720, 1750 cm$^{-1}$.

The above ketone (5.9 g) and ethyl 2-amino-4-phenyl-(2S)-butyrate (3.8 g) in 200 ml of chloroform containing di-n-butyltin dichloride (0.15 g) are refluxed using a water separator for 24 hours. The reaction mixture is evaporated to give a crude imine, which is used directly.

To the above imine (9.0 g) in 80 ml of methanol and 15 ml of acetic acid is added sodium cyanoborohydride (1.4 g). The reaction mixture is stirred 18 hours at room temperature, 3.0 ml of 12N hydrochloric acid are added and the reaction is evaporated. The residue in 75 ml of 10% aqueous sodium carbonate is extracted with 3×75 ml of methylene chloride. The combined organic portions are dried over magnesium sulfate and evaporated to give an oil. The diastereomeric amines are separated by flash column chromatography (silica gel, 3:1 toluene-ethyl acetate) to give 1-benzyloxycarbonylmethyl-3-(1-ethoxycarbonyl-3-phenyl-(1S)-propylamino)-3,4,5,6-tetrahydro-(3R)-1-benzazocin-2-1H-one, R$_f$=0.53 in 1:1 ethyl acetate-toluene, NMR (CDCl$_3$) 7.31 (5H, s), 7.18 (9H, m), 5.07 (2H, s), 4.36 (2H, s), 4.02 (2H, q, J=7), 1.11 (3H, t, J=7), and 1-benzyloxycarbonylmethyl-3-(1-ethoxycarbonyl-3-phenyl-(1S)-propylamino)-3,4,5,6-tetrahydro-(3S)-1-benzazocin-2-1H-one, R$_f$=0.50 in 1:1 ethyl acetate-toluene, NMR (CDCl$_3$) 7.35 (5H, s), 7.21 (9H, m), 5.18 (2H, s), 4.02 (2H, q, J=7), 1.01 (3H, t, J=7).

EXAMPLE 9

(a) Starting with 1,3,4,5,6,7-hexahydro-1-benzazonine-2-one [Ann. Chem., 586, 30 (1954)], 1-carboxymethyl-3-(1-carboxy-3-phenyl-(1S)-propylamino)-1,3,4,5,6,7-hexahydro-(3S)-1-benzazonin-2-one hydrochloride is prepared following the method described in Example 7a.

(b) 1-Carboxymethyl-3-(1-carboxy-3-phenyl-(1S)-propylamino)-1,3,4,5,6,7-hexahydro-(3R)-1-benzazonin-2-one hydrochloride is prepared following the method described in Example 7b.

(c) 1-Carboxymethyl-3-(1-ethoxycarbonyl-3-phenyl-(1S)-propylamino)-1,3,4,5,6,7-hexahydro-(3S)-1-benzazonin-2-one hydrochloride is prepared following the method described in Example 8a.

(d) 1-Carboxymethyl-3-(1-ethoxycarbonyl-3-phenyl-(1S)-propylamino)-1,3,4,5,6,7-hexahydro-(3R)-1-benzazonin-2-one hydrochloride is prepared following the method described in Example 8b.

EXAMPLE 10

A solution of 1-ethoxycarbonylmethyl-3,4,5,6-tetrahydro-1-benzazocin-2,3-1H-dione (7.0 g, 25.5 mmol) and ε-N-benzyloxycarbonyl-L-lysine ethyl ester (7.9 g, 25.5 mmol) in 300 ml of chloroform is refluxed with water separation in the presence of dibutyltin dichloride (0.40 g). After 2 hours the reaction is evaporated to give the crude imine (15.0 g), used without further purification.

To the above imine (15.0 g) in 8 ml of acetic acid and 100 ml of methanol is added sodium cyanoborohydride (3.5 g). The reaction is stirred overnight at room temperature and then quenched with 5 ml of 12N hydrochloric acid. After stirring 1 hour, the reaction is evaporated. The residue is adjusted to pH 9 with 2N sodium hydroxide and extracted with 3×150 ml of ethyl acetate. The combined organic portions are dried over magnesium sulfate and evaporated to give 3-[(5-benzyloxycarbonylamino-1-ethoxycarbonylpentyl)amino]-1-ethoxycarbonylmethyl-3,4,5,6-tetrahydro-1-benzazocin-2-1H-one as a mixture of diastereomers.

The above diastereomers are separated by flash column chromatography (silica gel, 1:1 toluene-ethyl acetate) to give the SR isomer (R$_f$=0.30) and the SS isomer (R$_f$=0.25).

EXAMPLE 11

A solution of 3-[(5-benzyloxycarbonylamino-1-(S)-ethoxycarbonylpentyl)amino]-1-ethoxycarbonylmethyl-3,4,5,6-tetrahydro-(3S)-1-benzazocin-2-1H-one (1.7 g) in 60 ml of methanol and 0.30 g of sodium hydroxide in 5 ml of water is stirred for 18 hours at room temperature. The reaction is evaporated. The residue in 50 ml of water is washed with 150 ml of ether, which is discarded. The aqueous layer is adjusted to pH 2.5 with 2N hydrochloric acid and concentrated to 15 ml to give a solid, which is collected by filtration to give 3-[(5-benzyloxycarbonylamino-1-(S)-carboxypentyl)amino]-1-carboxymethyl-3,4,5,6-tetrahydro-(3S)-1-benzazocin-2-1H-one hydrochloride, m.p. 122°–125° C., α$_D$=−70° (c=1.0, methanol). The SR diacid hydrochloride, m.p. 127°–129°, α$_D$=+101° (c=1.0, methanol) is prepared similarly.

EXAMPLE 12

A solution of 3-[(5-benzyloxycarbonylamino-1-(S)-carboxypentyl)amino]-1-carboxymethyl-3,4,5,6-tetrahydro-(3S)-1-benzazocin-2-1H-one (0.60 g) in 20 ml of water is hydrogenated at atmospheric pressure using 0.8 g of 10% palladium on carbon. The reaction is filtered and the filtrate is evaporated to give 3-[(5-amino-1-(S)-carboxypentyl)amino]-1-carboxymethyl-3,4,5,6-tetrahydro-(3S)-1-benzazocin-2-1H-one hydrochloride, m.p. 186°–188°, α$_D$=−83° (c=1.1, methanol). The SR diacid hydrochloride is prepared similarly; m.p. 182°–184°, α$_D$=+129°.

EXAMPLE 13

Preparation of 10,000 tablets each containing 10 mg of 1-carboxymethyl-3-(1-ethoxycarbonyl-3-phenylpropylamino)-3,4,5,6-tetrahydro-1-benzazocin-2-1H-one hydrochloride.

| Formula: | |
|---|---|
| 1-Carboxymethyl-3-(1-ethoxycarbonyl-3-phenyl-propylamino)-3,4,5,6-tetrahydro-1-benzazocin-2-1H—one hydrochloride | 100.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 14

Preparation of an injectable formulation containing 25 mg of 1-carboxymethyl-3-(1-ethoxycarbonyl-3-phenylpropylamino)-3,4,5,6-tetrahydro-1-benzazocin-2-1H-one hydrochloride:

| Formula | |
|---|---|
| 1-Carboxymethyl-3-(1-ethoxycarbonyl-3-phenylpropylamino)-3,4,5,6-tetrahydro-1-benzazocin-2-1H—one hydrochloride | 25.0 g |
| Propylparaben | 1.0 g |
| Water for injection q.s. | 5000.0 ml |

The active ingredient and preservative are dissolved in 3500 ml of water for injection and the solution is diluted to 5000 ml. The solution is filtered through a sterile filter and filled into injection vials under sterile conditions each vial containing 5 ml of the solution.

EXAMPLE 15

Preparation of 10,000 capsules each containing 20 mg of 1-carboxymethyl-3-(1-ethoxycarbonyl-3-phenylpropylamino)-3,4,5,6-tetrahydro-1-benzazocin-2-1H-one hydrochloride:

| Formula | |
|---|---|
| 1-Carboxymethyl-3-(1-ethoxycarbonyl-3-phenylpropylamino)-3,4,5,6-tetrahydro-1-benzazocin-2-1H—one hydrochloride: | 200.0 g |
| Lactose | 1,700.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg; using a capsule filling machine.

Analogously, tablets, injectable formulations or capsules are prepared from the remaining compounds of the invention, e.g. those illustrated by the examples herein, e.g.

(a) 1-carboxymethyl-3-(1-ethoxycarbonyl-3-phenyl-(1S)-propylamino)-3,4,5,6-tetrahydro-(3S)-1-benzazocin-2-1H-one hydrochloride;

(b) 3-[(5-amino-1-(S)-carboxypentyl)amino]-1-carboxymethyl-3,4,5,6-tetrahydro-(3S)-1-benzazocin-2-1H-one hydrochloride.

EXAMPLE 15

Illustrative of the invention, and according to the test methods previously described, the following angiotensin-converting enzyme inhibition data is obtained.

Compound of example 7a: in vitro test, $IC_{50} = 7.5 \times 10^{-9}$M.

Compound of example 8a: in vivo test, p.o. administration of 3.3 mg/kg (rat) gives 69% inhibition at 1 hr.

S,S compound of example 12: in vitro test, $IC_{50} = 2.7 \times 10^{-8}$M.

What is claimed is:

1. A compound of the formula

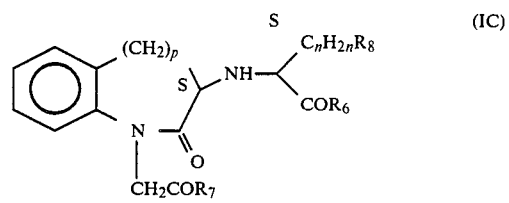

wherein
S represents the chirality,
n represents an integer from 1 to 4; p is the integer 3 or 4;
$R_8$ is hydrogen, amino, benzyloxycarbonylamino, phenyl unsubstituted or monosubstituted by lower alkyl, lower alkoxy, lower alkanoyloxy, halogen, hydroxy, or trifluoromethyl;
$R_6$ and $R_7$ independently represent hydroxy, lower alkoxy of up to 4 carbon atoms, benzyloxy or amino; or
a pharmaceutically acceptable salt thereof.

2. A compound of claim 1 wherein $(CH_2)_p$ represents propylene.

3. A compound of claim 1 being 1-carboxymethyl-3-(1-carboxy-3-phenyl-(1S)-propylamino)-3,4,5,6-tetrahydro-(3S)-1-benzazocin-2-1H-one or a pharmaceutically acceptable salt thereof.

4. A compound of claim 1 being 1-carboxymethyl-3-(1-carboxy-3-phenyl-(1S)-propylamino)-1,3,4,5,6,7-hexahydro-(3S)-1-benzazonin-2-one or a pharmaceutically acceptable salt thereof.

5. A compound of claim 1 being 1-carboxymethyl-3-(1-ethoxycarbonyl-3-phenyl-(1S)-propylamino)-1,3,4,5,6,7-hexahydro-(3S)-1-benzazonin-2-one or a pharmaceutically acceptable salt thereof.

6. A compound of claim 1 being 3-[(5-benzyloxycarbonylamino-1-(S)-carboxypentyl)amino]-1-carboxymethol-3,4,5,6-tetrahydro-(3S)-benzazocin-2-1H-one or pharmaceutically acceptable salt thereof.

7. 1-Carboxymethyl-3-(1-ethoxycarbonyl-3-phenyl-(1S)-propylamino)-3,4,5,6-tetrahydro-(3S)-1-benzazocin-2-1H-one or pharmaceutically acceptable salt thereof.

8. 3-[(5-Amino-1-(S)-carboxypentyl)amino]-1-carboxymethyl-3,4,5,6-tetrahydro-(3S)-1-benzazocin-2-1H-one or a pharmaceutically acceptable salt thereof.

9. A pharmaceutical composition suitable for oral or parenteral administration to mammals for the treatment or prevention of diseases responsive to inhibition of angiotensin-converting enzyme comprising an effective amount of a compound of claim 1 in combination with one or more pharmaceutically acceptable carriers.

10. A method of treating hypertensive or cardiac conditions in mammals which comprises administering to a mammal in need thereof an effective amount of a composition of claim 9.

11. A method of inhibiting angiotensin-converting enzyme which comprises administering to a mammal in need thereof an effective amount of a composition of claim 9.

* * * * *